US008895263B2

(12) United States Patent
Jordan et al.

(10) Patent No.: US 8,895,263 B2
(45) Date of Patent: Nov. 25, 2014

(54) METHODS FOR SUPPRESSING TOLL-LIKE RECEPTOR ACTIVITY

(75) Inventors: Jarrat Jordan, Radnor, PA (US);
Sun-Yung Jung, Radnor, PA (US);
Robert T. Sarisky, Yardley, PA (US);
Jessica Schreiter, Radnor, PA (US)

(73) Assignee: Janssen Biotech, Inc., Horsham, PA (US)

( * ) Notice: Subject to any disclaimer, the term of this patent is extended or adjusted under 35 U.S.C. 154(b) by 785 days.

(21) Appl. No.: 12/572,338

(22) Filed: Oct. 2, 2009

(65) Prior Publication Data

US 2010/0092462 A1 Apr. 15, 2010

Related U.S. Application Data

(60) Provisional application No. 61/102,033, filed on Oct. 2, 2008.

(51) Int. Cl.
| | | |
|---|---|---|
| C07H 21/04 | (2006.01) | |
| C07K 14/435 | (2006.01) | |
| C07K 14/705 | (2006.01) | |
| C12N 5/07 | (2010.01) | |
| C12P 21/02 | (2006.01) | |
| A61K 38/17 | (2006.01) | |
| C07K 16/28 | (2006.01) | |
| A61K 39/00 | (2006.01) | |

(52) U.S. Cl.
CPC ....... *C07K 16/2896* (2013.01); *A61K 2039/505* (2013.01); *A61K 38/177* (2013.01)
USPC ........ 435/69.1; 435/70.1; 435/325; 536/23.5; 530/350

(58) Field of Classification Search
None
See application file for complete search history.

(56) References Cited

U.S. PATENT DOCUMENTS

| | | | | |
|---|---|---|---|---|
| 8,066,981 | B2 * | 11/2011 | Kao et al. | 424/85.5 |
| 2006/0115475 | A1 | 6/2006 | Carton et al. | |
| 2007/0072202 | A1 | 3/2007 | Bates et al. | |
| 2007/0203064 | A1 | 8/2007 | Duffy et al. | |
| 2007/0211752 | A1 | 9/2007 | Warrier et al. | |

FOREIGN PATENT DOCUMENTS

WO  WO 2007/001332  1/2007

OTHER PUBLICATIONS

Rubenfeld et al., Incidence and Outcomes of Acute Lung Injury. New England J Med 353(16): 1685-1693, 2005.*
"Cystic fibrosis", www.nhlbi.nih.gov/health/health-topics/topics/cf/; downloaded Jan. 20, 2012; 2 pages.*
"Asthma" www.nhlbi.nih.gov/health/health-topics/topics/asthma/; downloaded Jan. 20, 2012; 2 pages.*
Skolnick et al. From genes to protein structure and function: novel applications of computational approaches in the genomic era. Trends in Biotech 18(1): 34-39, 2000.*
Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Pirollo et al. Targeted delivery of small interfering RNA: approaching effective cancer therapies. Cancer Res 68(5): 1247-1250, 2008.*
Phillips, A.J. The challenge of gene therapy and DNA delivery. J Pharmacy Pharmacol 53: 1169-1174, 2001.*
Vidal et al. Making sense of antisense. Eur J Cancer 41: 2812-2818, 2005.*
Elgert, K.D. Immunology: Understanding the immune system. New York: Wiley-Liss, 1996; p. 305.*
Takada et al. C-terminal LRRs of human Toll-like receptor 3 control receptor dimerization and signal transmission. Mol Immunol 44: 3633-3640, 2007.*
Alexopoulou, et al., "Recognition of double-stranded RNA and activation of NF-κb by Toll-like receptor 3," Nature, 413: 732-738 (2001).
Bergsbaken, et al., "Pyroptosis: host cell death and inflammation," Nature Reviews, 7: 99-109 (2009).
Brinkmann, et al., "The interaction between the ER membrane protein UNC93B and TLR3, 7, and 9 is crucial for TLR signaling," Journal of Cell Biology, 177: 265-275 (2007).
Dogusan, et al., "Double-Stranded RNA Induces Pancreatic β-Cell Apoptosis by Activation of the Toll-Like Receptor 3 and Interferon Regulatory Factor 3 Pathways," Diabetes, 57: 1236-1245 (2008).
Funami, et al., "The cytoplasmic 'linker region' in Toll-like receptor 3 controls receptor localization and signaling," International Immunology, 16: 1143-1154 (2004).
Anthony Gaspari, "Innate and adaptive immunity and the pathophysiology of psoriasis," 54: S67-S80 (2006).
Halse, et al., "Regulation of Glycogen Synthase by Glucose and Glycogen," Diabetes, 52: 9-15 (2003).
Hoffman, et al., "TLR-targeted therapeutics," Nature Review Drug Discovery, 4: 879-880 (2005).
Johnsen, et al., "Toll-like receptor 3 associates with c-Src tyrosine kinase on endosomes to initiate antiviral signaling," The EMBO Journal, 25: 3335-3346 (2006).
Kagan, et al., "TRAM couples endocytosis of Toll-like receptor 4 to the induction of interferon-β," Nature Immunology, 9: 361-368 (2008).
Kanzler, et al., "Therapeutic targeting of innate immunity with Toll-like receptor agonists and antagonists," Nature Medicine, 13: 552-559 (2007).
Kim, et al., "UNC93B1 delivers nucleotide-sensing toll-like receptors to endolysosomes," Nature, 452: 234-238 (2008).
Lancaster, et al., "The physiological regulation of toll-like receptor expression and function in humans," Journal of Physiology, 563: 945-955 (2005).

(Continued)

*Primary Examiner* — Bridget E Bunner
(74) *Attorney, Agent, or Firm* — Kirk Baumeister

(57) ABSTRACT

Agents interfering with translocation of Toll-like receptor 3 (TLR3), methods of making and using the foregoing are disclosed.

6 Claims, 3 Drawing Sheets

(56) References Cited

OTHER PUBLICATIONS

Lee, et al., "Necrotic neuronal cells induce inflammatory Schwann cell activation via TLR2 and TLR3: Implication in Wallerian degeneration," Biochemical and Biophysical Research Communications, 350: 742-747 (2006).
Le Goffic, et al., "Detrimental Contribution of the Toll-Like Receptor (TLR)3 to Influenza A Virus-Induced Acute Pneumonia," PloS Pathogens, 2: E53 (2006).
Liu, et al., "Structural Basis of Toll-Like Receptor 3 Signaling with Double-Stranded RNA," Science, 320: 379-381 (2008).
Morikawa, et al., "Identification of Toll-Like Receptor 3 as a Potential Therapeutic Target in Clear Cell Renal Cell Carcinoma," Clinical Cancer Research, 13: 5703-5709 (2007).
Pierre Miossec, "An update on the cytokine network in rheumatoid arthritis," Current Opinion in Rheumatology, 16: 218-222 (2004).
Nishiya, et al., "TLR3 and TLR7 are Targeted to the Same Intracellular Compartments by Distinct Regulatory Elements," The Journal of Biological Chemistry, 280-37107-37117 (2005).
Ogata, et al., "Cytokine and Anti-cytokine Therapies for Inflammatory Bowel Disease," Current Pharmaceutical Design, 9: 1107-1113 (2003).
Opelt, et al., "Overexpression of Toll-like Receptors 3 and 4 in Synovial Tissue From Patients with Early Rheumatoid Arthritis," Arthritis & Rheumatism, 58(12): 3684-3692 (2008).
Picha, et al., "Protein Engineering Strategies for Sustained Glucagon-Like peptide-1 Receptor-Dependent Control of Glucose Homeostasis," Diabetes, 57: 1926-1934 (2008).
Pries, et al., "Induction of c-Myc-dependent cell proliferation through toll-like receptor 3 in head and neck csncer," International Journal of Molecular Medicine, 21: 209-215 (2008).
Ranjith-Kumar, et al., "Single-Stranded Oligonucleotides Can Inhibit Cytokine Production Induced by Human Toll-Like Receptor 3," Molecular and Cellular Biology, 28(14): 4507-4519 (2008).
Ranjith-Kumar, et al., "Biochemical and Functional Analyses of the Human Toll-like Receptor 3 Ectodomain," The Journal of Biological Chemistry, 282(10): 7668-7678 (2007).
Ranjith-Kumar, et al., "Effects of Single Nucleotide Polymorphisms on Toll-like Receptor 3 Activity and Expression in Cultured Cells," Journal of Biological Chemistry, 282: 17696-17705 (2007).
Nina Rezaei, "Therapeutic targeting of pattern-recognition receptors," International Immunopharmacology, 6: 863-869 (2006).
Stumpp, et al., "DARPins: A true alternative to antibodies," Current Opinion in Drug Discovery & Development, 10(2): 153-159 (2007).
Sun, et al., "Structural and Functional Analyses of the Human Toll-like Receptor 3," The Journal of Biological Chemistry, 281: 11144-11151 (2006).
Tabeta, et al., "The *Unc93b1* mutation 3d disrupts exogenous antigen presentation and signaling via Toll-like receptors 3, 7 and 9," Nature Immunology, 7: 156-164 (2006).
Tabeta, et al., "Toll-like receptors 9 and 3 as essential components of innate immune defense against mouse cytomegalovirus infection," Proceedings of the National Academy of Science USA, 101: 3516-3521 (2004).
Takeda, et al., "C-terminal LRRs of human Toll-like receptor 3 control receptor dimerization and signal transmission," Molecular Immunology, 44: 5633-5640 (2007).
Takeda, et al., "Microbial recognition by Toll-like receptors," Journal of Dermatological Science, 34: 73-82 (2004).
Takahashi, et al., "A protein associated with Toll-like receptor (TLR) 4 (PRAT4A) is required for TLR-dependent immune responses," The Journal of Experimental Medicine, 204: 963-2976 (2007).
Takii, et al., "Enhanced expression of type 1 interferon and toll-like receptor-3 in primary biliary cirrhosis," Laboratory Investigations, 85: 908-920 (2005).
Tilg, et al., "Inflammatory Mechanisms in the Regulation of Insulin Resistance," 14(3-4): 222-231 (2008).
David M. Underhill, "Toll-like receptors and microbes take aim at each other," Current Opinion in Immunology, 16: 483-487 (2004).
Van Amersfoort, et al., "Receptors, Mediators, and Mechanisms Involved in Bacterial Sepsis and Septic Shock," Clinical Microbiology Reviews, 16(3): 379-414 (2003).
Vercammen, et al., "Sensing of Viral Infection and Activation of Innate Immunity by Toll-Like Receptor 3," Clinical Microbiology Reviews, 21(1): 13-25 (2008).
Ingrid Wickelgren, "Targeting the Tolls," Science, 312: 184-187 (2006).
Yang, et al., "Toll-like Receptor 3 and Geographic Atrophy in Age-Related Macular Degeneration," The New England Journal of Medicine, 359: 1456-1463 (2008).
Yilmaz, et al., "Identification and sequence analysis of chicken Toll-like receptors," Immunogenetics, 56: 743-753 (2005).
Zhang, et al., "TLR3 Deficiency in Patients with Herpes Simplex Encephalitis," Science, 317: 1522-1527 (2007).
Zhou, et al., "Recognition of Double-Stranded RNA by TLR3 Induces Severe Small Intestinal Injury in Mice," Journal of Immunology, 178: 4548-4556 (2007).
Supplemental EP Search Report dated Mar. 20, 2012, for 09818568.9.
Duffy, et al., "Down modulation of human TLR3 function by a monoclonal antibody," Cell Immunology, 248(2): 103-114 (2007).
Edwards, et al., "Targeting the NF-kappaB pathway in asthma and chronic obstructive pulmonary disease," Pharmacological Therapy, 121(1): 1-13 (2009).
Eunjeong Yang, et al., "Cloning of TLR3 isoform," Yonsei Meidcal Journal, 45(2): 359-361 (2004).
PCT International Search Report dated Apr. 23, 2010, for PCT/US09/59383.

* cited by examiner

Figure 1

```
Hu_TLR3      101 LKVLNLQHNELSQLSDKTFAFCTNLTELHLMSNSIQKIKNNPFVKQKNLI  150
                 |||||||||||||||||||||||||||||||||||||||||||||||||
Hu_TLR3_Iso  101 LKVLNLQHNELSQLSDKTFAFCTNLTELHLMSNSIQKIKNNPFVKQKNLI  150

Hu_TLR3      151 TIDLSHNGLSSTKLGTQVQLENLQELLLSNNKIQALKSEELDIFANSSLK  200
                 |||||||||||||||||||||||||||||||||||||||||||||||||
Hu-TLR3_Iso  151 TIDLSHNGLSSTKLGTQVQLENLQELLLSNNKIQALKSEELDIFANSSLK  200

Hu_TLR3      201 KLELSSNQIKEFSPGCFHAIGRLFGLFLNNVQLG?SLTEKLCLELANTSI  250
                 |||||||||||||||||||||||||||||||||||||||||||||||||
Hu_TLR3_Iso  201 KLELSSNQIKEFSPGCFHAIGRLFGLFLNNVQLG?SLTEKLCLELANTSI  250

Hu_TLR3      251 RNLSLSNSQLSTTSNTTFLGLKWTNLTMLDLSYNNLNVVGNDSFAWLPQL  300
                 |||||||||||||||||||||||||||||||||||||
Hu_TLR3_Iso  251 RNLSLSNSQLSTTSNTTFLGLKWTNLTMLDLSYNNLNV------------  298

Hu_TLR3      301 EYFFLEYNNIQHLFSHSLHGLFNVRYLNLKRSFTKQSISLASLPKIDDFS  350

Hu_TLR3_Iso  288 --------------------------------------------------  288

Hu_TLR3      351 FQWLKCLEHLNMEDNDIPGIKSNMFTGLINLKYLSLSNSFTSLRTLTNET  400
                 |||||||||||||||||||||||||||||| |||||||||||||||||
Hu_TLR3_Iso  289 --WLKCLEHLNMEDNDIPGIKSNMFTGLINLKYLSLSNSFTSLRTLTNET  336

Hu_TLR3      401 FVSLAHSPLHILNLTKNKISKIESDAFSWLGHLEVLDLGLNEIGQELTGQ  450
                 |||||||||||||||||||||||||||||||||||||||||||||||||
Hu-TLR3_Iso  337 FVSLAHSPLHILNLTKNKISKIESDAFSWLGHLEVLDLGLNEIGQELTGQ  386
```

Region Amplified by PCR

METHODS FOR SUPPRESSING TOLL-LIKE RECEPTOR ACTIVITY

CROSS-REFERENCE TO RELATED APPLICATIONS

This application claims priority to U.S. Provisional Application No. 61/102,033, filed 2 Oct. 2008, the entire contents of which is incorporated herein by reference in its entirety.

FIELD OF THE INVENTION

The present invention relates to agents that suppress Toll-like receptor translocation and activity, and methods of using the foregoing.

BACKGROUND OF THE INVENTION

Toll-like receptors (TLRs) regulate activation of the innate immune response and influence the formation of adaptive immunity by detecting and initiating signal transduction cascades in response to bacterial, viral, parasitic, and in some cases host-derived ligands (Lancaster et al., J. Physiol. 563: 945-955, 2005). Members of the TLR family TLR1, TLR2, TLR4 and TLR6 are located on the plasma membrane and activate downstream signaling pathways in response to ligands including protein or lipid components of bacteria and fungi. TLR3, TLR7 and TLR9 are preferentially localized intracellularly, and respond to dsRNA, ssRNA and unmethylated CpG DNA, respectively.

TLRs signal through adaptor molecules myeloid differentiation factor 88 (MyD88), Toll/IL-1 receptor domain containing adaptor inducing interferon-beta (TRIF) and TRIF-related adaptor molecule (TRAM), initiating signaling pathways involving JNK/p38 kinase, interferon-regulatory factors (IFN) IFN-3, IFN-5 and IFN-7, and NF-kB, leading to the production of pro-inflammatory cytokines (Romagne, Drug Discov. Today 12:80-87, 2007). TLR3 regions critical for receptor signaling have been identified. Mutations in residues involved in protein glycosylation, disulfide bond formation, loop 2 and leucine rich repeat (LRR) sequences result in signaling deficient TLR3 (Ranjith-Kumar et al., J. Biol. Chem. 282:7668-7678, 2007; Ranjith-Kumar et al., J. Biol. Chem. 282:17696-17705, 2007; Sun et al., J. Biol. Chem. 281:11144-11151, 2006; Takada et al, Mol. Immunol. 44:3633-3640, 2007). Crystal structure of a complex between two murine TLR3 extracellular domains and TLR3 ligand dsRNA further revealed ligand binding amino acids and regions critical for proper folding and dimerization of TLR3 (Liu et al., Science 320:379-81, 2008). TLR3 may also be regulated via alternative splicing. A soluble form of TLR3 was cloned in chicken (Yilmaz et al., Immunogenetics 56:743-53, 2005), and a human TLR3 mRNA encoding a splice variant with alternative splicing of TLR3 exon 4 resulting in 192 bp in frame deletion has been identified (Yang et al., Immunogenetics 56:743-53, 2005). The functional significance of the TLR3 variants described is unknown.

Dysregulation of TLR signaling is believed to cause a multitude of problems, and therapeutic strategies are in development towards this axis (Hoffman et al., Nat. Rev. Drug Discov. 4:879-880, 2005; Rezaei, Int. Immunopharmacol. 6:863-869, 2006; Wickelgren, Science 312:184-187, 2006). For example, antagonists of TLR4 and TLRs 7 and 9 are in clinical development for severe sepsis and lupus, respectively (Kanzler et al., Nat. Med. 13:552-559, 2007).

TLR3 signaling is activated by dsRNA, mRNA or RNA released from necrotic cells upon inflammation or virus infection. TLR3 activation results in induced secretion of interferons and pro-inflammatory cytokines, which have been associated with pathogen infections, and shown to contribute to a spectrum of inflammatory, immune-mediated and autoimmune diseases, for example, asthma, chronic obstructive pulmonary disease, psoriasis, septic shock, rheumatoid arthritis, inflammatory bowel disease such as Crohn's disease and ulcerative colitis, and type I diabetes (Tabeta et al., Proc. Natl. Acad. Sci. 101:3516-3521, 2004; Underhill, Curr. Opin. Immunol. 16:483-487, 2004; Gaspari, J. Am. Acad. Dermatol. 54:S67-80, 2006; Van Amersfoort et al., Clin. Microbiol. Rev. 16:379-414, 2003; Miossec et al., Curr. Opin. Rheumatol. 16:218-222, 2004; Ogata and Hibi, Curr. Pharm. Res. 9:1107-1113, 2003; Takeda and Akira, J. Derm. Sci. 34:73-82, 2004; Doqusan et al., Diabetes 57:1236-1245, 2008).

TLR3 expression has been shown to correlate with inflammatory responses associated with pathological conditions such as primary biliary cirrhosis of liver tissues (Takii et al., Lab Invest. 85:908-920, 2005). Furthermore, TLR3 was found overexpressed in joints of patients with rheumatoid arthritis (Ospelt et al., Arthritis Rheum. 58:3684-92, 2008). TLR3 plays a key role in the immune response upon virus infection. For example, TLR3 deficient animals exhibit a survival advantage over wild type animals upon influenza A virus infection, with the enhancement of survival correlating with reduced levels of pro-inflammatory mediators (Le Goffic et al., PloS Pathog. 2:E53, 2006). TLR3 deficient animals are also protected from rotavirus infection-induced mucosal epithelial breakdown (Zhou et al. J. Immunology 178:4548-4556, 2007). In humans, a dominant-negative TLR3 allele has been associated with increased susceptibility to Herpes Simplex encephalitis upon primary infection with HSV-1 (Zheng et al., Science 317:1522-7 2007).

In necrotic conditions, the release of intracellular content including endogenous mRNA triggers secretion of cytokines, chemokines and other factors that induce local inflammation, facilitate clearance of dead cell remnants and repair the damage. Necrosis often perpetuates inflammatory processes, contributing to chronic or exaggerated inflammation (Bergsbaken et al., Nature Reviews 7:99-109, 2009). Activation of TLR3 at the site of necrosis may contribute to these aberrant inflammatory processes and generate a further pro-inflammatory positive feedback loop via the TLR3 ligands released. Down-modulation of TLR3 activation may also represent a novel treatment strategy for oncologic indications including renal cell carcinomas and head and neck squamous cell carcinomas (Morikawa et al., Clin. Cancer Res. 13:5703-5709, 2007; Pries et al., Int. J. Mol. Med. 21: 209-15, 2008). Also, a previously characterized $TLR^{3L423F}$ allele resulting in reduced TLR3 activity was associated with protection against advanced "dry" age-related macular degeneration (Yang et al., N. Engl. J. Med. 359:1456-63, 2008), indicating that TLR3 antagonist agents may be beneficial in this disease.

Pathologies associated with inflammatory conditions and others, such as those associated with infections, have significant health and economic impacts. Yet, despite advances in many areas of medicine, comparatively few treatment options and therapies are available for many of these conditions.

Thus, a need exists to suppress TLR3 activity to treat TLR3-associated conditions.

BRIEF DESCRIPTION OF THE DRAWINGS

FIG. 1. Alignment of protein sequences of TLR3Δ64 and TLR3. TLR3Δ64 has a 64 amino acid deletion corresponding to amino acids 289-353 in the wild type TLR3 polypeptide.

Top: human TLR3 residues 101-450 of SEQ ID NO: 4. Bottom: TLR3Δ64 residues 78-363 of SEQ ID NO: 2. Residue numbering is according to TLR3 sequence of SEQ ID NO: 4.

Figure 2:
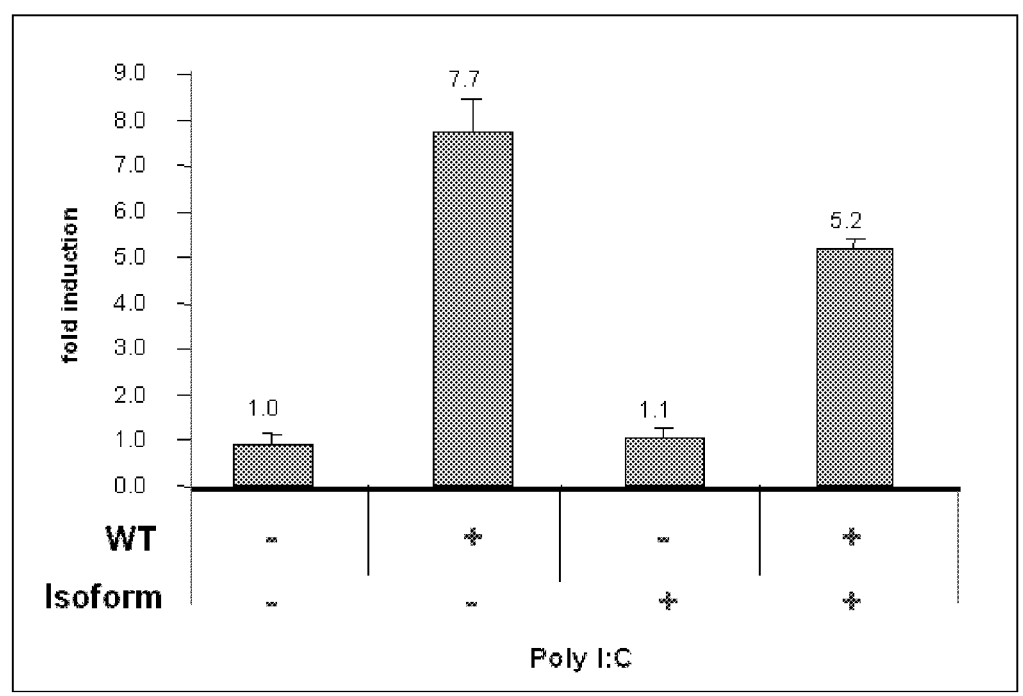

FIG. 2: TLR3Δ64 is deficient in signaling upon poly(I:C)-stimulation and exerts suppressive effect on poly (I:C)-induced activation of NF-κB by wild type TLR3.

Figure 3:
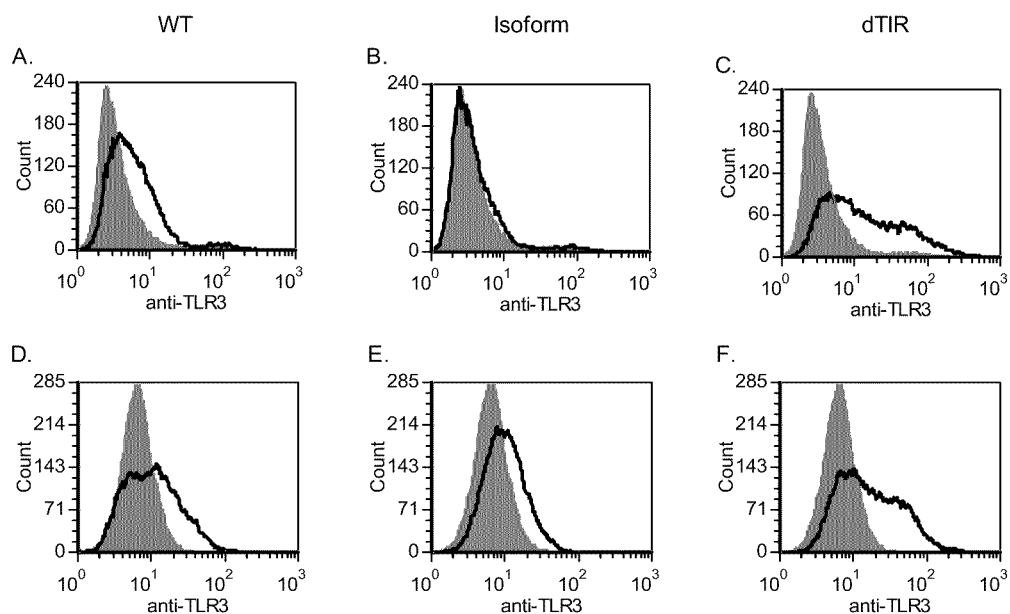

FIG. 3: Surface (A, B, C) and intracellular (D, E, F) expression of wild type TLR3 (solid line), TLR3Δ64 (dotted line), and TLR3ΔTIR (dashed line) by FACS. Isoform control is indicated in gray.

SUMMARY OF THE INVENTION

One aspect of the invention is a method for suppressing Toll-like receptor 3 (TLR3) activity in a subject in need thereof comprising administering to the subject an agent that interferes with translocation TLR3.

Another aspect of the invention is a method of treating or preventing an inflammatory condition comprising administering a therapeutically effective amount of an agent to a patient in need thereof wherein the agent interferes with translocation of TLR3 for a time sufficient to treat or prevent the inflammatory condition.

Another aspect of the invention is a method of treating or preventing a necrotic condition comprising administering a therapeutically effective amount of an agent to a patient in need thereof wherein the agent interferes with translocation of TLR3 for a time sufficient to treat or prevent the necrotic condition.

Another aspect of the invention is a method of treating or preventing an infectious disease comprising administering a therapeutically effective amount of an agent to a patient in need thereof wherein the agent interferes with translocation of TLR3 for a time sufficient to treat or prevent the infectious disease.

Another aspect of the invention is a method of treating or preventing a cardiovascular disease comprising administering a therapeutically effective amount of an agent to a patient in need thereof wherein the agent interferes with translocation of TLR3 for a time sufficient to treat or prevent the cardiovascular disease.

Another aspect of the invention is a method of treating or preventing type 1 or type 2 diabetes comprising administering a therapeutically effective amount of an agent to a patient in need thereof wherein the agent interferes with translocation of TLR3 for a time sufficient to treat or prevent the type 1 or type 2 diabetes.

Another aspect of the invention is a method of treating or preventing a cancer comprising administering a therapeutically effective amount of an agent to a patient in need thereof wherein the agent interferes with translocation of TLR3 for a time sufficient to treat or prevent the cancer.

Another aspect of the invention is a method of treating or preventing a rheumatoid disease comprising administering a therapeutically effective amount of an agent to a patient in need thereof wherein the agent interferes with translocation of TLR3 for a time sufficient to treat or prevent the rheumatoid disease.

Another aspect of the invention is a method of treating or preventing a pulmonary disease comprising administering a therapeutically effective amount of an agent to a patient in need thereof wherein the agent interferes with translocation of TLR3 for a time sufficient to treat or prevent the pulmonary disease.

Another aspect of the invention is a method of treating or preventing a neurological disorders comprising administering a therapeutically effective amount of an agent to a patient in need thereof wherein the agent interferes with translocation of TLR3 for a time sufficient to treat or prevent the neurological disorder.

DETAILED DESCRIPTION OF THE INVENTION

All publications, including but not limited to patents and patent applications, cited in this specification are herein incorporated by reference as thought fully set forth.

It is to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

Although any methods and materials similar or equivalent to those described herein can be used in the practice for testing of the present invention, exemplary materials and methods are described herein. In describing and claming the present invention, the following terminology will be used.

As used herein, the term "suppressing" or "suppress" means partially or totally blocking stimulation, decreasing, preventing, delaying activation, inactivating, or down regulating TLR3 activity. Suppression of Toll-like receptor activity is achieved when the Toll-like receptor activity value relative to the control is 50-80%, optionally 25-50% or 0-25%, where control samples are assigned a relative TLR3 activity value of 100%.

The term "agent" means polypeptides, peptides or proteins, fusion proteins, peptidomimetics, antibodies, nucleic acids, oligonucleotides, synthetic oligonucleotides and the like that bind TLR3, suppress TLR3 activity and have at least one of the following characteristics: interfere with or alter TLR3 translocation, interfere with or alter TLR3 subcellular localization, interfere with co-localization of TLR3 with its ligand. The agent can be identified using assays for TLR3 activity or assays to evaluate translocation or subcellular localization of TLR3, alone or together with evaluating localization of TLR3 ligand. Examples of agents include a TLR3 variant polypeptide having an amino acid sequence shown in SEQ ID NO: 1, a TLR3 variant polypeptide having an amino acid sequence shown in SEQ ID NO: 2, or a polypeptide comprising an amino acid sequence shown in SEQ ID NO: 3.

The term "TLR3 activity" or "activity" as used herein refers to any activities occurring as a result of ligand binding to TLR3. TLR3 ligands include dsRNA, poly(I:C), and endogenous mRNA, e.g., endogenous mRNA released from necrotic cells. An exemplary TLR3 receptor activation results in activation of NE-κB in response to the TLR3 ligand. NE-κB activation can be assayed using a reporter-gene assay upon induction of the receptor with poly(I:C) (Alexopoulos et al., Nature 413:732-738, 2001; Hacker et al., EMBO J. 18:6973-6982, 1999). Another exemplary TLR3 receptor activation results in activation of interferon response factors (IRF-3, IRF-7) in response to TLR3 ligand. TLR3-mediated IRF activation can be assayed using a reporter gene driven by an interferon-stimulated response element (ISRE). Another exemplary TLR3 receptor activation results in secretion of pro-inflammatory cytokines and chemokines, for example TNF-α, IL-6, IL-8, IL-12, IP-10 and RANTES. The release of cytokines and chemokines from cells, tissues or in circulation can be measured using well-known immunoassays, such as an ELISA immunoassay.

The term "wild type" or "WT" refers to a gene or gene product that has the characteristics of that gene or gene product when isolated from a naturally occurring source. A wild type gene is that which is most frequently observed in a population and is thus arbitrarily designated the "normal" or "reference" or "wild type" form of the gene.

The term "TLR3 variant" refers to a polypeptide or polynucleotide that differs from a reference "wild type" TLR3 polypeptide or polynucleotide and may or may not retain essential properties. Generally, differences in sequences of the reference polypeptide and the variant are closely similar overall and, in many regions, identical. A variant and reference polypeptide may differ in amino acid sequence by one or more modifications for example, substitutions, insertions or deletions. A substituted or inserted amino acid residue may or may not be encoded by the genetic code, and the substitution, insertion or deletion may be either conservative or non-conservative. Insertions and deletions can be of varying length, for example between 1-64 amino acids. A variant of a polypeptide may be naturally occurring such as an allelic splice variant, or it may be a variant that is not known to occur naturally.

As used herein, the term "dominant negative" or "dominant negative protein" refers to the product of a dominant negative mutant gene. The term "dominant negative mutant gene" refers to a gene encoding a protein product that interferes with function of the wild type or other variants of the same gene or gene product. The term "dominant negative" is not intended to be limited in the manner in which the dominant negative protein interferes with functioning of the wild type protein or in the manner in which the dominant negative protein is made. The dominant negative protein can be a splice variant of TLR3 or fragments thereof. It can suppress TLR3 activity by interfering with translocation of TLR3 or interfering with co-localization of TLR3 and its ligands. The dominant negative protein can be produced synthetically. The term "dominant negative" is also intended to include splice variant or mutant gene products that provide partial suppression or function alteration, and it is not intended to require total suppression.

As used herein the phrases "interferes with translocation" and "interferes with localization" can be interchangeably used and refer to partially or completely altering, hindering, or intervening with translocation or subcellular localization, or altering the rate of such translocation of TLR3.

As used herein the terms "translocate", "translocates", "transolcated", "translocation" or "translocating" refer to the movement of TLR3 from one intracellular compartment to another, e.g., from one subcellular compartment to another subcellular compartment. The movement of TLR3 may occur for example, from the endoplasmic reticulum (ER) to the Golgi complex, from the ER to the endosome, from the ER to the lysosome, from the plasma membrane to the endosome, and from the plasma membrane to the lysosome. The movement of TLR3 can be dependent on any of the well-characterized vesicular transport systems, for example via clathrin-coated vesicles, caveolin-dependent movement, or CopI- or CopII-dependent movement (Mancias and Goldberg, Traffic 6:278-85, 2005; van der Goot and Gruenberg, Trends Cell. Biol. 16:514-521, 2006; Parton and Richards, Traffic 4:724-38, 2003), or on a novel mechanism yet to be characterized.

Methods of detecting translocation and intracellular localization of TLR3, co-localization of TLR3 with its ligands, for example poly(I:C) or ODN2006, other toll-like receptors, for example TLR7 or TLR9, any cell structure or cellular protein, for example endoplasmic reticulum, endosome, lysosome or plasma membrane and resident proteins thereof, and methods of detecting concentration of TLR3 on the cell surface or intracellulary are well known. Exemplary methods are fluorescent microscopy of tagged or intrinsically fluorescent polypeptides or molecules, cell fractionation and cell sorting methods (Meyer and Teruel, Trends in Cell Biol. 13:101-106, 2003; Giepmans et al., Science 312:217-224, 2006, Watson et al., Advanced Drug Delivery Reviews 57:43-61, 2005; Kumar et al., Adv. Biochem. Eng. Biotechnol. 106:1-18, 2007; Tung et al., Clin. Lab. Med. 27:453-468, 2007). For example, cellular localization of overexpressed TLR3 can be detected with specific anti-TLR3 antibody followed by a secondary antibody conjugated to a fluorescent molecule using fluorescent microscopy. TLR3 localization can also be evaluated using FACS assay utilizing anti-TLR3 antibodies.

As used herein, "subcellular compartment" refers to any sub-structural macromolecular component of the cell whether it is made of protein, lipid, carbohydrate, or nucleic acid. It could be a macromolecular assembly or an organelle (a membrane delimited cellular component). Examples of subcellular compartments are cytoplasm, nucleus, plasma membrane, Golgi, trans-Golgi Network, lysosme, endosome, endoplasmic reticulum, extracellular space, and mitochondrion.

As used herein, the term "co-localization" or "co-localized" refers two or more molecules having identical or overlapping localization in the cell. Co-localization of molecules and proteins can be detected using fluorescent microscopy in fixed or living cells. For example, TLR3 and its ligand poly (I:C) can be co-localized in cells using fluorescently-labeled poly(I:C), anti-TLR3 primary antibodies and Alexa Fluor® 647-conjugated secondary antibodies. Methods of co-localization of cellular molecules are well known.

"Surface expression" refers to the amount of TLR3 polypeptides that are found at the plasma membrane.

An "endosomal compartment" or "endosome" is an intracellular vesicular compartment e.g., an organelle that is involved in the export of chemical substances including biomolecules such as lipids and proteins from the cells, internalization and recycling of such biomolecules from the plasma membrane, to and from subcellular compartments, and translocation of such biomolecules between subcellular compartments. Examples of endosomal compartments include the perinuclear recycling compartment (PRC), the recycling endosomes, the secretory vesicles, and the trans-Golgi network (TGN).

The term "antibody" refers to a molecule specifically binding to an antigen, and includes dimeric, trimeric and multimeric antibodies, and chimeric, humanized and fully human antibodies. Also, an antibody may be a whole antibody or a functional fragment of an antibody molecule, such as a fragment retaining at least its antigen binding function, and include Fab, F(ab'), F(ab')$_2$, scFv, dsFv, and diabody. For example, antibody fragments may be obtained using proteolytic enzymes (e.g., a whole antibody is digested with papain to produce Fab fragments, and pepsin treatment results in the production of F(ab')$_2$ fragments). Techniques for the preparation and use of the various antibodies are well known in the art (Ausubel, et al., ed., Current Protocols in Molecular Biology, John Wiley & Sons, Inc., NY 1987-2001; Sambrook, et al., Molecular Cloning: A Laboratory Manual, $2^{nd}$ Edition, Cold Spring Harbor, N.Y., 1989; Harlow and Lane, Antibodies, a Laboratory Manual, Cold Spring Harbor, N.Y., 1989; Colligan, et al., ed., Current Protocols in Immunology, John Wiley & Sons, Inc., NY 1994-2001; Colligan et al., Current Protocols in Protein Science, John Wiley & Sons, NY, NY, 1997-2001).

The term "ligand" refers to an oligonucleotide, synthetic or endogenous RNA moiety, peptide or polypeptide that binds to, or complexes with, a human TLR3 receptor or variant thereof, such as poly(I:C) (Alexopoulou et al., Nature 413: 732-738, 2001) or ODN2006 (Ranjith-Kumar et al., Mol Cell Biol. 28:4507-19, 2008). The ligand may be an antagonist, inhibitor, suppressor, agonist, stimulator or activator, or the like, of TLR3.

The present invention relates to agents that interfere with TLR3 translocation and uses of such agents. The invention is based, at least in part, on the unexpected discovery that a naturally occurring splice variant of TLR3, herein named TLR3Δ64, was found to interfere with TLR3 translocation and activity. For example, amino acid residues 289-352 of the extracellular domain of the wild type TLR3 (GenBank Acc. No. NP 0032565.1; SEQ ID NO: 4) were identified to be responsible for exit of TLR3 from the ER, for endosomal and plasma membrane localization, and for ability of TLR3 to co-localize with its ligands. Exemplary agents include a TLR3 variant TLR3Δ64 polypeptide having an amino acid sequence shown in SEQ ID NO: 1, an extracellular domain of TLR3Δ64 polypeptide having an amino acid sequence shown in SEQ ID NO: 2, and a polypeptide comprising amino acids 289-352 of the WT TLR3 shown in SEQ ID NO: 3. Pro-inflammatory cytokine secretion and NF-kB activation resulting from TLR3 activation has been associated with a spectrum of human conditions. Thus, these agents are useful as research reagents and therapeutic agents.

One embodiment of the invention is a method of suppressing toll-like receptor 3 (TLR3) activity in a subject in need therefor, comprising administering to the subject an agent that interferes with translocation of TLR3. TLR3 localized in the endoplasmic reticulum is believed to be translocated to dsRNA-containing endosomes in response to dsRNA stimulation, a process that requires the ER-resident protein Unc93B1 (Johnsen et al., EMBO J. 25:3335-3346, 2006; Kim et al., Nature 452:234-238, 2008). TLR3 residues implicated in regulating receptor translocation are the transmembrane domain (amino acids 707-728 of SEQ ID NO: 4) that binds Unc93B1 and the cytosolic linker region (amino acids 727-749 of SEQ ID NO: 4) that also has been demonstrated to be responsible for endosomal localization of TLR3 (Funami et al., Int. Immunol. 16:1143-1154, 2004; Nishiva et al., J. Biol. Chem. 280:37107-37117, 2005; US2006/0265767A1). UNC93B1 mutations simultaneously abolish normal ligand-induced translocation and signaling of all currently known nucleic acid-sensing TLRs TLR3, TLR7 and TLR9 (Tabeta et al., Nat. Immunol. 7: 156-164, 2006; Brinkmann et al., J. Cell. Biol. 177:265-275, 2007). Other proteins and pathways implicated in trafficking and signaling of TLR family members include PRAT4A, an ER resident that associates with TLR9 (Takahashi et al., J. Exp. Med. 204:2963-2976, 2007) and dynamin, a GTPase essential for clathrin-dependent coated vesicle formation. Dynamin inhibition prevented LPS-induced internalization of TLR4, a process required for type I interferon production (Kagan et al., Nat. Immunol. 9:361-368, 2008). Thus, normal translocation of TLRs is required for receptor signaling, and therefore agents modulating TLR transolcation can have therapeutic utility. Specific modulation of TLR3 translocation may have the benefit of bypassing the pleiotrophic effects resulting from the inhibition of molecules involved in the translocation of multiple receptors or widely used vesicular transport mechanisms, such as UNC93B1 and dynamin, resulting in less substantial affects on host immunity of the therapeutic.

While not wishing to bound to any particular theory, it is thought that the agent of the invention interferes with TLR3 translocation by binding to and forming complexes with wild type TLR3 and subsequently masking or interfering with TLR3 translocation signals, or by preventing TLR3 dimerization required for proper receptor activity including perhaps internalization. The agent interfering with TLR3 translocation can be an antibody or antibody fragment reactive with the extracellular domain of TLR3. It is contemplated that an antibody reactive with TLR3 could interfere with TLR3 translocation and activity by masking the signal encoded by these amino acids in regulating TLR3 translocation. Exemplary antibodies are antibodies reactive with the wild type TLR3 polypeptide amino acids 289-352 shown in SEQ ID NO: 3.

It is possible to modify the structure of the polypeptides or fragments of the invention for such purposes as enhancing substrate specificity, stability, solubility, and the like. For example, a modified polypeptide can be produced in which the amino acid sequence has been altered, such as by amino acid substitution, deletion, or addition. An isolated replacement of a leucine with an isoleucine or valine, an aspartate with a glutamate, a threonine with a serine, or a similar replacement of an amino acid with a structurally related amino acid (i.e., conservative mutations) will, in some instances but not all, not have a major effect on the biological activity of the resulting molecule. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981). Whether a change in the amino acid sequence of a polypeptide or fragment thereof results in a functional homolog can be readily determined by assessing the ability of the modified polypeptide or fragment to produce a response in a fashion similar to the unmodified polypeptide or fragment using the assays described herein. Peptides, polypeptides or proteins in which more than one replacement has taken place can readily be tested in the same manner.

The agent interfering with TLR3 translocation can be conjugated to a second polypeptide to form a fusion protein that can confer desirable properties, for example increased stability. Exemplary fusion proteins can be formed by conjugating together a TLR3 variant TLR3Δ64 polypeptide having an amino acid sequence shown in SEQ ID NO: 1, an extracellular domain of TLR3Δ64 polypeptide having an amino acid sequence shown in SEQ ID NO: 2, and a polypeptide comprising an amino acid sequence shown SEQ ID NO: 3, and an alternative scaffold such as designed ankyrin repeat protein (DARPins) (Stumpp and Amstutz, Curr. Opin. Drug Discov. Devel. 10:153-159, 2007), MIMETIBODY™ construct (Picha et al. Diabetes 57:1926-1934, 2008), other protein domains or peptides specific for TLR3. Fusion proteins may generally be generated using either recombinant nucleic acid methods or by chemical synthesis methods well known in the art.

The present invention provides methods of treating or preventing a number of mammalian disease states where suppression of TLR3 activity is desirable by interfering with TLR3 translocation, for example inflammatory conditions, infectious diseases, necrotic conditions, cardiovascular disease, type I diabetes, type II diabetes, cancer, rheumatoid disease, pulmonary disease and neurological disorders.

Agents interfering with TLR3 translocation can be used in the methods of prevention and treatment of the invention. For example, TLR3 variant TLR3Δ64 polypeptide having an amino acid sequence shown in SEQ ID NO: 1, an extracellular domain of TLR3Δ64 polypeptide having an amino acid sequence shown in SEQ ID NO: 2, and a polypeptide comprising an amino acid sequence shown SEQ ID NO: 3 are useful.

The methods of the invention may be used to treat a subject in need of treatment. "Subject" refers to any animal, preferably a human patient, livestock, or domestic pet. Without wishing to be bound by any particular theory, it is believed that the therapeutic benefit of agents that interfere with TLR3 translocation will be due to the ability of such agents to inhibit TLR3 ligand-induced NF-kB and/or IRF3 activation ultimately resulting in the secretion of pro-inflammatory chemokines and cytokines, and type I interferons, respectively, whereas the dysregulation of the aforementioned immunomodulatory molecules is known to be involved in many inflammatory conditions.

Amounts of a given agent sufficient to treat or prevent a given condition can be readily determined. In the methods of the invention, the agent may be administered singly or in combination with at least one other molecule. Such additional molecules may be molecules with a therapeutic benefit not mediated by TLR3 receptor signaling. Antibiotics, antivirals, palliatives and compounds that reduce cytokine levels or activity are examples of such additional molecules. Such additional molecules may be an antibody, MIMETIBODY™ construct, oligonucleotide, or small molecule specific for TLR3 or another TLR receptor. "In combination with" as used herein means that the described agents can be administered to a subject together in a mixture, concurrently as single agents or sequentially as single agents in any order.

In another embodiment, the invention provides a method of treating or preventing an inflammatory condition comprising administering a therapeutically effective amount of an agent to a patient in need wherein the agent interferes with translocation of TLR3 for a time sufficient to treat or prevent the inflammatory condition.

Generally, inflammatory conditions, infection-associated conditions or immune-mediated inflammatory disorders that may be prevented or treated by the methods of the invention include those mediated by cytokines and those conditions which result wholly or partially from activation of TLR3 or signaling through the TLR3 pathway. Examples of such inflammatory conditions include sepsis-associated conditions, inflammatory bowel diseases, autoimmune disorders, inflammatory disorders and infection-associated conditions.

One example of such inflammatory conditions is sepsis-associated conditions may include systemic inflammatory response syndrome (SIRS), septic shock or multiple organ dysfunction syndrome (MODS). While not wishing to be bound by an particular theory, it is believed that treatment with agents interfering with TLR3 translocation can provide a therapeutic benefit by extending survival times in patients suffering from sepsis-associated inflammatory conditions or prevent a local inflammatory event (e.g., in the lung) from spreading to a systemic condition, by potentiating innate antimicrobial activity, by demonstrating synergistic activity when combined with antimicrobial agents, by minimizing the local inflammatory state contributing to the pathology, or any combination of the foregoing. Such intervention may be sufficient to permit additional treatment (e.g., treatment of underlying infection or reduction of cytokine levels) necessary to ensure patient survival.

Another example of such inflammatory conditions is inflammatory bowel diseases. The inflammatory bowel disease may be Crohn's disease or ulcerative colitis. Those skilled in the art will recognize other inflammatory bowel disease of known or unknown etiology that cause inflammation of the bowel.

Another example of such inflammatory conditions is an inflammatory pulmonary condition. Exemplary inflammatory pulmonary conditions include infection induced pulmonary conditions including those associated with viral, bacterial, fungal, parasite or prion infections; allergen induced pulmonary conditions; pollutant induced pulmonary conditions such as asbestosis, silicosis, or berylliosis; gastric aspiration induced pulmonary conditions, immune dysregulation, genetically induced inflammatory pulmonary conditions such as cystic fibrosis, and physical trauma induced pulmonary conditions, such as ventilator injury. These inflammatory conditions also include asthma, emphysema, bronchitis, COPD, sarcoidosis, histiocytosis, lymphangiomyomatosis, acute lung injury, acute respiratory distress syndrome, chronic lung disease, bronchopulmonary dysplasia, community-acquired pneumonia, nosocomial pneumonia, ventilator-associated pneumonia, sepsis, viral pneumonia, influenza infection, parainfluenza infection, human metapneumovirus infection, respiratory syncitial virus infection and *aspergillus* or other fungal infections.

Exemplary infection-associated inflammatory diseases may include viral or bacterial pneumonia, including severe pneumonia, cystic fibrosis, bronchitis, airway exacerbations and acute respiratory distress syndrome (ARDS). Such infection-associated conditions may involve multiple infections such as a primary viral infection and a secondary bacterial infection.

Other inflammatory conditions and neuropathies, which may be prevented or treated by the method of the invention are those caused by autoimmune diseases. These conditions and neuropathies also include multiple sclerosis, sclerosis lupus erythematous, and neurodegenerative and central nervous system (CNS) disorders including Alzheimer's disease, Parkinson's disease, Huntington's disease, bipolar disorder and Amyotrophic Lateral Sclerosis (ALS), liver diseases including fibrosis, hepatitis C virus (HCV) and hepatitis B virus (HBV), diabetes and insulin resistance, cardiovascular disorders including stroke and myocardial infarction, arthritis, rheumatoid arthritis, psoriatic arthritis and juvenile rheumatoid arthritis (JRA), osteoporosis, osteoarthritis, pancreatitis, fibrosis, encephalitis, psoriasis, Giant cell arteritis, ankylosing spondolytis, autoimmune hepatitis, human immunodeficiency virus (HIV), inflammatory skin conditions, transplant, cancer, allergies, endocrine diseases, wound repair, other autoimmune disorders, airway hyper-responsiveness and cell, virus, or prion-mediated infections or disorders.

Exemplary cancers may include at least one malignant disease in a cell, tissue, organ, animal or patient, including, but not limited to, at least one of: leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodyplastic syndrome (MDS), a lymphoma, Hodgkin's disease, a malignant lymphoma, non-Hodgkin's lymphoma, Burkitt's lymphoma, multiple myeloma, Kaposi's sarcoma, colorectal carcinoma, pancreatic carcinoma, renal cell carcinoma, breast cancer, nasopharyngeal carcinoma, malignant histiocytosis, paraneoplastic syndrome/hypercalcemia of malignancy, solid tumors, adenocarcinomas, squamous cell carcinomas, sarcomas, malignant melanoma, particularly metastatic melanoma, hemangioma, metastatic disease, cancer related bone resorption, cancer related bone pain, and the like.

Exemplary cardiovascular diseases may include at least one cardiovascular disease in a cell, tissue, organ, animal, or patient, including, but not limited to, at least one of cardiac stun syndrome, myocardial infarction, congestive heart failure, stroke, ischemic stroke, hemorrhage, arteriosclerosis, atherosclerosis, restenosis, diabetic atherosclerotic disease, hypertension, arterial hypertension, renovascular hypertension, syncope, shock, syphilis of the cardiovascular system, heart failure, cor pulmonale, primary pulmonary hypertension, cardiac arrhythmias, atrial ectopic beats, atrial flutter, atrial fibrillation (sustained or paroxysmal), post perfusion syndrome, cardiopulmonary bypass inflammation response, chaotic or multifocal atrial tachycardia, regular narrow QRS tachycardia, specific arrhythmias, ventricular fibrillation, His bundle arrhythmias, atrioventricular block, bundle branch block, myocardial ischemic disorders, coronary artery disease, angina pectoris, myocardial infarction, cardiomyopathy, dilated congestive cardiomyopathy, restrictive cardiomyopathy, valvular heart diseases, endocarditis, pericardial disease, cardiac tumors, aordic and peripheral aneurysms, aortic dissection, inflammation of the aorta, occulsion of the abdominal aorta and its branches, peripheral vascular disorders, occulsive arterial disorders, peripheral atherosclerotic disease, thromboangitis obliterans, functional peripheral arterial disorders, Raynaud's phenomenon and disease, acrocyanosis, erythromelalgia, venous diseases, venous thrombosis, varicose veins, arteriovenous fistula, lymphederma, lipedema, unstable angina, reperfusion injury, post pump syndrome, ischemia-reperfusion injury, and the like.

Exemplary neurological diseases may include at least one neurologic disease in a cell, tissue, organ, animal or patient, including, but not limited to, at least one of: neurodegenerative diseases, multiple sclerosis, migraine headache, AIDS dementia complex, demyelinating diseases, such as multiple sclerosis and acute transverse myelitis; extrapyramidal and cerebellar disorders such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; Progressive supranucleo Palsy; structural lesions of the cerebellum; spinocerebellar degenerations, such as spinal ataxia, Friedreich's ataxia, cerebellar cortical degenerations, multiple systems degenerations (Mencel, Dejerine-Thomas, Shi-Drager, and Machado-Joseph); systemic disorders (Refsum's disease, abetalipoprotemia, ataxia, telangiectasia, and mitochondrial multisystem disorder); demyelinating core disorders, such as multiple sclerosis, acute transverse myelitis; and disorders of the motor unit such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; Senile Dementia of Lewy body type; Wernicke-Korsakoff syndrome; chronic alcoholism; Creutzfeldt-Jakob disease; Subacute sclerosing panencephalitis, Hallerrorden-Spatz disease; and Dementia pugilistica, and the like.

Exemplary fibrotic conditions may include liver fibrosis (including but not limited to alcohol-induced cirrhosis, viral-induced cirrhosis, autoimmune-induced hepatitis); lung fibrosis (including but not limited to scleroderma, idiopathic pulmonary fibrosis); kidney fibrosis (including but not limited to scleroderma, diabetic nephritis, glomerular nehpritis, lupus nephritis); dermal fibrosis (including but not limited to scleroderma, hypertrophic and keloid scarring, burns); myelofibrosis; neurofibromatosis; fibroma; intestinal fibrosis; and fibrotic adhesions resulting from surgical procedures. In such a method, the fibrosis can be organ specific fibrosis or systemic fibrosis. The organ specific fibrosis can be associated with at least one of lung fibrosis, liver fibrosis, kidney fibrosis, heart fibrosis, vascular fibrosis, skin fibrosis, eye fibrosis, bone marrow fibrosis or other fibrosis. The lung fibrosis can be associated with at least one of idiopathic pulmonary fibrosis, drug induced pulmonary fibrosis, asthma, sarcoidosis or chronic obstructive pulmonary disease. The liver fibrosis can be associated with at least one of cirrhosis, schistomasomiasis or cholangitis. The cirrhosis can be selected from alcoholic cirrhosis, post-hepatitis C cirrhosis, primary biliary cirrhosis. The cholangitis is sclerosing cholangitis. The kidney fibrosis can be associated with at least one of diabetic nephropathy or lupus glomeruloschelerosis. The heart fibrosis can be associated with at least one type of myocardial infarction. The vascular fibrosis can be associated with at least one of postangioplasty arterial restenosis, or atherosclerosis. The skin fibrosis can be associated with at least one of burn scarring, hypertrophic scarring, keloid, or nephrogenic fibrosing dermatopathy. The eye fibrosis can be associated with at least one of retro-orbital fibrosis, postcataract surgery or proliferative vitreoretinopathy. The bone marrow fibrosis can be associated with at least one of idiopathic myelofibrosis or drug induced myelofibrosis. The other fibrosis can be selected from Peyronie's disease, Dupuytren's contracture or dermatomyositis. The systemic fibrosis can be selected from systemic sclerosis and graft versus host disease.

The "therapeutically effective amount" of the agent effective in the treatment or prevention of conditions where suppression of TLR3 activity is desirable can be determined by standard research techniques. For example, the dosage of the agent which will be effective in the treatment or prevention of inflammatory condition such as Crohn's Disease and ulcerative colitis can be determined by administering the agent to an animal model of Crohn's Disease and ulcerative colitis, such as animals that have ingested dextran sulfate sodium (DSS) (Okayasu et al., Gastroenterology 98:694-702, 1990).

In addition, in vitro assays can optionally be employed to help identify optimal dosage ranges. Selection of a particular effective dose can be determined (e.g., via clinical trials) by a skilled artisan based upon the consideration of several factors. Such factors include the disease to be treated or prevented, the symptoms involved, the patient's body mass, the patient's immune status and other factors known by the skilled artisan. The precise dose to be employed in the formulation will also depend on the route of administration, and the seriousness of the disease-related wasting, and should be decided according to the judgment of the practitioner and each patient's circumstances. Effective doses can be extrapolated from dose-response curves derived from in vitro or animal model test systems. The dose of the agent to be administered to a patient, such as a human, is rather widely variable and can be subject to independent judgment. It is often practical to administer the daily dose of the agent at various hours of the day. However, in any given case, the amount of the agent administered will depend on such factors as the solubility of the agent, the formulation used, patient condition (such as weight), and/or the route of administration.

The mode of administration for therapeutic use of the agent of the invention may be any suitable route that delivers the agent to the host. The proteins, protein fragments, fusion proteins, antibodies and antibody fragments and pharmaceutical compositions of these agents are particularly useful for parenteral administration, e.g., intradermal, intramuscular, intraperitoneal, intravenous, subcutaneous or intranasal.

The agent of the invention may be prepared as pharmaceutical compositions containing an effective amount of the agent as an active ingredient in a pharmaceutically acceptable carrier. The term "carrier" refers to a diluent, adjuvant, excipient, or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the agent of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected. Actual methods for preparing parenterally administrable compositions are well known and are described in more detail in, for example, "Remington's Pharmaceutical Science", 15$^{th}$ ed., Mack publishing Company, Easton, Pa.

The present invention is further described with reference to the following examples. These examples are merely to illustrate aspects of the present invention and are not intended as limitations of this invention.

Example 1

TLR3Δ64 is Expressed in Primary Cells

TLR3Δ64 is a naturally occurring TLR3 variant reported earlier having a deletion of 64 amino acids corresponding to amino acids 289-353 in the wild type TLR3 polypeptide (GenBank acc. No. NP_0032565.1; SEQ ID NO: 4) (Yang et al. Immunogenetics. 56:743-53, 2005). The function of the variant is not known. In this study, TLR3Δ64 sequence was identified and the variant shown to be expressed in primary human cells, including human bronchial epithelial cells.

Expression was assessed by PCR using oligonucleotide primers 5'GATCTGTCTCATAATGGCTTGTCA 3' (SEQ ID NO: 5) and 5'GTTTATCAATCCTGTGAACATAT 3' (SEQ ID NO: 6) according to Yang et al., (Yonesei Medical Journal 45:359-361, 2004) using standard procedures (Molecular Cloning: a Laboratory Manual, 2$^{nd}$ ed. Vols 1-3, Cold Spring Harbor Laboratory, 1989; Current protocols in molecular biology, Ausubel, ed. John Wiley & Sons, Inc, New York, 1997). In brief, primary normal human astrocytes (NHA) were obtained and cultured as recommended by the supplier (Lonza, Ltd). A bronchial epithelial cell line (BEAS-2B) was obtained from ATCC (cat# CRL-9609™ and cultured as recommended for normal human bronchial epithelial cells (NHBE) by Lonza. NHBE cells were cultured to full differentiation as previously described (Krunkosky et al., Am. J. Respir. Cell mol. Biol. 22:685-692, 2000; Krunkosky et al., Microb. Patholog. 42:98-103, 2007). HEK293T cells, both non-transfected and transiently transfected with wild type TLR3 or TLR3Δ64 were used as a positive control and cultured in DMEM (Gibco) containing 10% FBS (Gibco). RNA was isolated and purified from all cell types using the Qiagen RNeasy kit following the manufacturer's instructions. Reverse transcription was performed using the BIO-RAD iScript cDNA synthesis kit. Products were separated on a 1% agarose gel. Results from RT-PCR showed the presence of two bands in NHA and BEAS-2B cells migrating at approximately 684 bp and 492 bp (data not shown). The 684 bp band corresponded to the WT TLR3 and the 492 bp band corresponded to the TLRΔ64, and the bands co-migrated with bands from control samples amplified from HEK293T cells expressing either the WT or the TLR3Δ64 construct, respectively. Expression of TLR3Δ64 was also assessed in NHBE cells. Results from RT-PCR showed presence of a 492 bp amplification product in NHBE cells that corresponded to TLR3Δ64, in addition to a 684 bp product that corresponded to the WT TLR3. The amplified approximately 492 bp band from NHA, BEAS-2B and NHBE cells was excised and gel-purified using Qiagen's QIAquick Gel Extraction kit. Purified DNA was cloned into Invivogen's TOPO pCR4 vector and sequenced using ABI's BigDye Terminator. The resulting nucleotide sequence was translated to show the amino acid sequence of the protein using the EMBOSS software suite (Rice, Longden et al. 2000). Sequencing confirmed that the approximately 492 bp isolated fragment represented TLRΔ64 and contained the reported 192 bp deletion when compared to the WT TLR3 (Yang et al., Yonesei Medical journal 45:359-361, 2004). Alignment of protein sequences of TLR3Δ64 and TLR3 is shown in FIG. 1.

Example 2

TLR3Δ64 is Deficient in Signaling and Modulates TLR3 Activity

In order to assess potential functional differences between the wild type TLR3 and TLR3Δ64, ability of TLR3Δ64 to activate downstream signaling pathways was assessed. HEK293T cells were transiently transfected with plasmids containing WT TLR3 and/or TLR3Δ64 cDNA in pcDNA3.1, stimulated with poly (I:C), and the induction of NF-κB was measured using a luciferase reporter gene assay (FIG. 2). WT TLR3 demonstrated a 7.7 fold induction of TLR3-dependent NF-κB activity induced by poly(I:C), whereas there was no induction of TLR3-dependent NF-κB activation when cells were transfected with the TLR3Δ64 construct. Co-transfection of both WT TLR3 and TLR3Δ64 demonstrated a dominant negative effect for TLR3Δ64. TLR3Δ64 suppressed WT TLR3 activity by 30%.

The full-length human TLR3 cDNA (Genbank Acc. NO. U88879) was amplified from human dendritic cells and cloned into the pcDNA3.1. Using the primers (Forward: 5'-CGA TCT TTC CTA CAA CAA CTT AAA TGT GTG GCT AAA ATG TTT GGA GCA CC-3' (SEQ ID NO: 7) and Reverse: 5'-GGT GCT CCA AAC ATT TTA GCC ACA CAT TTA AGT TGT TGT AGG AAA GAT CG-3' SEQ ID NO: 8) from IDT, Coralville, Iowa) and recombinant pfu, the mutagenesis reaction was performed on the WT TLR3 cDNA, cloned in pcDNA3.1 DpnI (NEB, Ipswich, Mass.) digested, and transformed into E. coli. Transformant colonies were picked and grown in overnight cultures containing ampicillin. Plasmids were then purified and sequenced (BigDye terminator v3.1, Applied Biosystems, Foster City, Calif.) to confirm presence of correct sequence corresponding to TLR3Δ64. HEK293T cells were seeded in white Costar 96-well plates at a density of $4.2 \times 10^4$ cells/well in Dulbecco's Modified Eagle Medium (DMEM) supplemented with 10% FBS. After 24 hours, the cells were transfected with plasmids containing the firefly luciferase reporter pNifty-Luc (30 ng; Invivogen), renilla reporter phRL-TK (5 ng; Promega), and 0.6 ng/well of plasmids containing TLR3 or TLR3Δ64 constructs using the lipofectamine transfection method (Invitrogen) as designated in FIG. 2. Twenty-four hours post-transfection, media was aspirated and DMEM with or without poly (I:C) (1 µg/ml) was added to appropriate sets of transfected cells to induce TLR3-dependent NF-κB activity. After an additional incubation for 24 h, the cells were harvested using the Dual Glo luciferase assay system reagents (Promega). Luminescence was quantified using the FLUOstar OPTIMA Plate Reader (BMG Labtech, Inc.). cDNA sequence of the full length TLR3 is shown in SEQ ID NO: 9 and the cDNA sequence of the TLR3Δ64 is shown in SEQ ID NO: 10.

Example 3

Deficient Trafficking of TLRΔ64

We studied surface expression, subcellular localization and protein stability of TLR3Δ64 to evaluate mechanism of suppression of the WT TLR3 activity by TLR3Δ64. Surface expression of TLR3Δ64 and TLR3 were studied by FACS analysis of overexpressed proteins in HEK293T cells. Contrary to wild type TLR3 localizing partially on cell surface (FIG. 3A), TLR3Δ64 was not detected on the surface of HEK293T cells (FIG. 3B). Both proteins, however, were present intracellularly (FIGS. 3D, 3E). A TLR3 mutant lacking the C-terminal signaling domain (TLR3ΔTIR) required for TLR3 signal transduction and shown to be deficient in inducing NF-κB activation was used as an additional control in this experiment (Matsumoto et al., Biochem. Biophys. Res. Commun. 293:1364-1369, 2002). Despite the absence of the TIR signaling domain and inability to activate downstream signaling, TLR3ΔTIR was found both on the surface and intracellularly (FIGS. 3C, 3F). Thus, lack of activity is not predictive of correct localization of TLR3.

Deficient plasma membrane expression of TLR3Δ64 could result from decreased stability of TLR3Δ64. To this end, TLR3Δ64 and WT TLR3 steady state levels were compared after 48 hours post-transfection with corresponding construct in HEK293T cells by Western blot. TLR3Δ64 exhibited comparable steady-state stability to wild type TLR3 (data not shown). Actin was used as a loading control in the experiment. Thus, reduced stability is not the cause for lack of TLR3Δ64 surface expression.

TLR3Δ64 subcellular localization and possible co-localization with its substrate poly(I:C) was evaluated using confocal microscopy. WT TLR3 demonstrated punctuate cytosolic fluorescence that partially co-localized with fluorescence of TLR3 ligand poly(I:C). In addition to punctuate cytosolic fluorescence comparable to that of WT TLR3, TLR3ΔTIR demonstrated diffuse reticular fluorescence, and as WT TLR3, partial overlap with the ligand poly(I:C). Fluorescence of TLR3Δ64 was distinct from that of the WT TLR3, demonstrating reticular diffuse cytosolic staining, usually indicative of ER localization. TLR3Δ64 did not co-localize with poly(I:C) in the cells. TLR3Δ64 co-localization with a second ligand, ODN2006, a ssDNA found to be a potent inhibitor of TLR3 signaling was also evaluated (Ranjith-Kumar et al., Mol. Cell. Biol. 28:4507-19, 2008). Confocal microscopy showed that TLR3Δ64 was retained in the reticular intracellular compartment and failed to co-localize with vesicular ODN2006 whereas two controls, TLR3 and TLR3ΔTIR did co-localized with ODN2006. Thus, TLR3Δ64 conferred translocation defect on the receptor retaining it in the reticular intracellular compartment indicative of the ER, prevented its surface expression, translocation to the endosomal compartment and co-localization with its ligands, in this example poly(I:C) and ODN2006, two structurally and functionally distinct ligands, the former being a dsRNA agonist, and the latter a ssDNA antagonist of TLR3.

For Western blot, HEK293T cells expressing recombinant wild type or TLR3Δ64 were lysed in M-PER (Pierce Inc.) in the presence of Complete mini protease inhibitors (Roche Inc.) and sonicated to shear chromosomal DNA. Equal amounts of proteins from each sample, as determined by a BCA protein assay (Pierce Inc.), were separated on NuPAGE 4-12% bis-tris gel and blotted onto a PVDF membrane. The anti-TLR3 antibody IMG-315A (Imgenex) was used as primary antibody for Western analysis. Blots were developed with peroxidase conjugated secondary antibodies using SuperSignal West Femto Maximum Sensitivity Substrate (Pierce Inc.). For confocal analysis, HEK293T cells were transiently transfected as described above. Following a 24 h incubation the media was replaced and cells were seeded onto 12 mm coverslips coated with rat tail collagen I (BD Biosciences, San Diego, Calif.). After an additional 24 h incubation, cells were either treated with 2 µM of 3' modified FITC ODN 2006 (InvivoGen), 2 µg/ml Poly(I-C) (Amersham) that was fluorescently labeled using a Cy5-labeling kit as recommended by the manufacturer (Mirus Bio Corp.), or left untreated for 24 h. All cells on coverslips were then gently washed with PBS and transferred to wells containing 4% paraformaldehyde diluted in PBS and fixed for 30 min at room temperature. After 2 washes in PBS containing 0.05% Tween®20 [PBST], the cells were permeabilized for 15 min with 0.1% TX-100 diluted in PBS, washed once more, blocked 30 min with Image-iT®FX signal enhancer (Invitrogen), and further blocked an additional 2 h at room temperature with 1× blocking buffer (Sigma). The permeabilized and fixed cells were incubated with a goat anti-human TLR3 polyclonal antibody (3 µg/ml) AF1487 (R&D Systems Inc.), diluted in blocking buffer overnight at 4° C., then washed 4 times with PBST and incubated for 1 h at room temperature with Alexa Fluor® 647-conjugated donkey anti-goat IgG (2 µg/mL; Invitrogen) containing 1 µg/mL of DAPI (Sigma) diluted in 1× blocking buffer. The coverslips were carefully washed an additional 4 times in PBST followed by one wash in distilled water, inverted and placed on microscope slides containing Citifluor mounting media (Ted Pella) and sealed with nail polish. Cells were imaged using a 60× oil immersion objective (NA=1.4) and optical slices of 0.2 µm were captured using an UltraVIEW ERS confocal microscope (PerkinElmer). For FACS analysis, HEK293T cells were transiently transfected with plasmids containing TLR3Δ64 or WT TLR3 cDNA in pcDNA3.1 as described. 24 h hours post-transfection, the cells were washed in cold staining buffer (SB) consisting of PBS+3% FBS+0.04% NaN$_3$. Viability by trypan blue exclusion was >95%. FITC-labeled polyclonal goat anti-TLR3 (R&D FAB1487F) at 1 µg/200,000 cells was incubated for 30 minutes at 4° C. Prior to intracellular staining, cells were fixed and permeabilized by incubation in Cytofix/Cytoperm buffer (BD Biosciences). Data acquisition was performed on a FACSCalibur flow cytometer (BD Biosciences) and data analysis was performed using FCS Express (De Novo Software, Ontario, Canada).

Example 4

TLR3Δ64 does not Interfere with RNA Binding Regions

The amino acids deleted in TLR3Δ64 on the WT TLR3 extracellular domain were mapped on the model based on the published crystal structure of a complex between two murine TLR3 extracellular domains and dsRNA to better understand potential structural and functional issues that may arise as a consequence of the deletion (Liu et al., Science 320:379-381, 2008). Based on modeling, amino acids 289-353 of WT TLR3 that are deleted in TLR3Δ64 were not found to directly coincide with the mapped RNA binding regions. Instead, the loss of amino acids 289-353 would be expected to shorten the region between the N- and C-terminal domains on each TLR3-ECD that are responsible for dsRNA binding. It has been demonstrated earlier that deletion of some domains, specifically some LRR repeat domains, between the N- and C-terminal dsRNA binding regions abolished activity of TLR3, presumably by perturbing relative positions of the two dsRNA binding sites. However, deletion of LRR11, encompassing aa 299-322 in WT TLR3 and partially overlapping amino acids 289-353 that are deleted in TLR3Δ64 did not abolish TLR3 function (Takada et al, Mol. Immunol. 44:3633-3640, 2007). Thus, TLR3 amino acids 289-353 were shown to control translocation, surface expression and co-localization of TLR3 with its ligands. The functions of these amino acids described in the invention could not be predicted based on previous knowledge of crystal structure or information from functional mutagenesis studies (Ranjith-Kumar et al., J. Biol. Chem. 282:7668-7678, 2007; Ranjith-Kumar et al., J. Biol. Chem. 282: 17696-17705, 2007; Sun et al., J. Biol. Chem. 281:11144-51, 2006; Takada et al, Mol. Immunol. 44:3633-3640, 2007).

TLR3 coordinates (PDB ID: 3CIY) were downloaded from the protein data bank. Residues 289-352 of wild type TLR3 were mapped on the model indicating the region absent in TLR3Δ64. Molecular graphics images were produced using the UCSF Chimera package from the Resource for Biocomputing, Visualization, and Informatics at the University of California, San Francisco (supported by NIH P41 RR-01081.

The present invention now being fully described, it will be apparent to one of ordinary skills in the art that many changes and modifications can be made thereto without departing from the spirit or scope of the appended claims. The specific embodiments described herein are offered by way of example only, and the invention is to be limited by the terms of the appended claims, along with the full scope of equivalents to which such claims are entitled, and the invention is not to be limited by the specific embodiments that have been presented herein by way of example.

What is claimed is:

1. A method of interfering with translocation of toll-like receptor 3 (TLR3) in vitro, comprising transfecting into a cell expressing TLR3 a cDNA that encodes an agent that interferes with translocation of TLR3, wherein the agent is a TLR3 variant comprising a polypeptide having the amino acid sequence shown in SEQ ID NO: 1 or SEQ ID NO: 2.

2. The method of claim 1, wherein the cell is a HEK293T cell.

3. The method of claim 1, wherein the agent interferes with surface expression of TLR3.

4. The method of claim 1, wherein the agent interferes with translocation of TLR3 from the endoplasmic reticulum.

5. The method of claim 1, wherein the agent interferes with translocation of TLR3 to the endosome.

6. The method of claim 1, wherein the agent interferes with co-localization of TLR3 with its ligand.

* * * * *

SEQUENCE LISTING

```
<160> NUMBER OF SEQ ID NOS: 11

<210> SEQ ID NO 1
<211> LENGTH: 817
<212> TYPE: PRT
<213> ORGANISM: Homo sapiens

<400> SEQUENCE: 1

Ser Thr Thr Lys Cys Thr Val Ser His Glu Val Ala Asp Cys Ser His
1               5                   10                  15

Leu Lys Leu Thr Gln Val Pro Asp Asp Leu Pro Thr Asn Ile Thr Val
            20                  25                  30

Leu Asn Leu Thr His Asn Gln Leu Arg Arg Leu Pro Ala Ala Asn Phe
        35                  40                  45

Thr Arg Tyr Ser Gln Leu Thr Ser Leu Asp Val Gly Phe Asn Thr Ile
    50                  55                  60

Ser Lys Leu Glu Pro Glu Leu Cys Gln Lys Leu Pro Met Leu Lys Val
65                  70                  75                  80

Leu Asn Leu Gln His Asn Glu Leu Ser Gln Leu Ser Asp Lys Thr Phe
                85                  90                  95

Ala Phe Cys Thr Asn Leu Thr Glu Leu His Leu Met Ser Asn Ser Ile
            100                 105                 110

Gln Lys Ile Lys Asn Asn Pro Phe Val Lys Gln Lys Asn Leu Ile Thr
        115                 120                 125

Leu Asp Leu Ser His Asn Gly Leu Ser Ser Thr Lys Leu Gly Thr Gln
    130                 135                 140

Val Gln Leu Glu Asn Leu Gln Glu Leu Leu Leu Ser Asn Asn Lys Ile
145                 150                 155                 160

Gln Ala Leu Lys Ser Glu Glu Leu Asp Ile Phe Ala Asn Ser Ser Leu
                165                 170                 175

Lys Lys Leu Glu Leu Ser Ser Asn Gln Ile Lys Glu Phe Ser Pro Gly
            180                 185                 190

Cys Phe His Ala Ile Gly Arg Leu Phe Gly Leu Phe Leu Asn Asn Val
        195                 200                 205

Gln Leu Gly Pro Ser Leu Thr Glu Lys Leu Cys Leu Glu Leu Ala Asn
```

```
            210                 215                 220
Thr Ser Ile Arg Asn Leu Ser Leu Ser Asn Ser Gln Leu Ser Thr Thr
225                 230                 235                 240

Ser Asn Thr Thr Phe Leu Gly Leu Lys Trp Thr Asn Leu Thr Met Leu
                245                 250                 255

Asp Leu Ser Tyr Asn Asn Leu Asn Val Trp Leu Lys Cys Leu Glu His
                260                 265                 270

Leu Asn Met Glu Asp Asn Asp Ile Pro Gly Ile Lys Ser Asn Met Phe
                275                 280                 285

Thr Gly Leu Ile Asn Leu Lys Tyr Leu Ser Leu Ser Asn Ser Phe Thr
                290                 295                 300

Ser Leu Arg Thr Leu Thr Asn Glu Thr Phe Val Ser Leu Ala His Ser
305                 310                 315                 320

Pro Leu His Ile Leu Asn Leu Thr Lys Asn Lys Ile Ser Lys Ile Glu
                325                 330                 335

Ser Asp Ala Phe Ser Trp Leu Gly His Leu Glu Val Leu Asp Leu Gly
                340                 345                 350

Leu Asn Glu Ile Gly Gln Glu Leu Thr Gly Gln Glu Trp Arg Gly Leu
                355                 360                 365

Glu Asn Ile Phe Glu Ile Tyr Leu Ser Tyr Asn Lys Tyr Leu Gln Leu
                370                 375                 380

Thr Arg Asn Ser Phe Ala Leu Val Pro Ser Leu Gln Arg Leu Met Leu
385                 390                 395                 400

Arg Arg Val Ala Leu Lys Asn Val Asp Ser Ser Pro Ser Pro Phe Gln
                405                 410                 415

Pro Leu Arg Asn Leu Thr Ile Leu Asp Leu Ser Asn Asn Asn Ile Ala
                420                 425                 430

Asn Ile Asn Asp Asp Met Leu Glu Gly Leu Glu Lys Leu Glu Ile Leu
                435                 440                 445

Asp Leu Gln His Asn Asn Leu Ala Arg Leu Trp Lys His Ala Asn Pro
                450                 455                 460

Gly Gly Pro Ile Tyr Phe Leu Lys Gly Leu Ser His Leu His Ile Leu
465                 470                 475                 480

Asn Leu Glu Ser Asn Gly Phe Asp Glu Ile Pro Val Glu Val Phe Lys
                485                 490                 495

Asp Leu Phe Glu Leu Lys Ile Ile Asp Leu Gly Leu Asn Asn Leu Asn
                500                 505                 510

Thr Leu Pro Ala Ser Val Phe Asn Asn Gln Val Ser Leu Lys Ser Leu
                515                 520                 525

Asn Leu Gln Lys Asn Leu Ile Thr Ser Val Glu Lys Lys Val Phe Gly
                530                 535                 540

Pro Ala Phe Arg Asn Leu Thr Glu Leu Asp Met Arg Phe Asn Pro Phe
545                 550                 555                 560

Asp Cys Thr Cys Glu Ser Ile Ala Trp Phe Val Asn Trp Ile Asn Glu
                565                 570                 575

Thr His Thr Asn Ile Pro Glu Leu Ser Ser His Tyr Leu Cys Asn Thr
                580                 585                 590

Pro Pro His Tyr His Gly Phe Pro Val Arg Leu Phe Asp Thr Ser Ser
                595                 600                 605

Cys Lys Asp Ser Ala Pro Phe Glu Leu Phe Phe Met Ile Asn Thr Ser
                610                 615                 620

Ile Leu Leu Ile Phe Ile Phe Ile Val Leu Leu Ile His Phe Glu Gly
625                 630                 635                 640
```

```
Trp Arg Ile Ser Phe Tyr Trp Asn Val Ser Val His Arg Val Leu Gly
            645                 650                 655

Phe Lys Glu Ile Asp Arg Gln Thr Glu Gln Phe Glu Tyr Ala Ala Tyr
            660                 665                 670

Ile Ile His Ala Tyr Lys Asp Lys Asp Trp Val Trp Glu His Phe Ser
            675                 680                 685

Ser Met Glu Lys Glu Asp Gln Ser Leu Lys Phe Cys Leu Glu Glu Arg
690                 695                 700

Asp Phe Glu Ala Gly Val Phe Glu Leu Glu Ala Ile Val Asn Ser Ile
705                 710                 715                 720

Lys Arg Ser Arg Lys Ile Ile Phe Val Ile Thr His His Leu Leu Lys
                725                 730                 735

Asp Pro Leu Cys Lys Arg Phe Lys Val His His Ala Val Gln Gln Ala
                740                 745                 750

Ile Glu Gln Asn Leu Asp Ser Ile Ile Leu Val Phe Leu Glu Glu Ile
            755                 760                 765

Pro Asp Tyr Lys Leu Asn His Ala Leu Cys Leu Arg Arg Gly Met Phe
        770                 775                 780

Lys Ser His Cys Ile Leu Asn Trp Pro Val Gln Lys Glu Arg Ile Gly
785                 790                 795                 800

Ala Phe Arg His Lys Leu Gln Val Ala Leu Gly Ser Lys Asn Ser Val
                805                 810                 815

His
```

<210> SEQ ID NO 2
<211> LENGTH: 616
<212> TYPE: PRT
<213> ORGANISM: Homo sapiens

<400> SEQUENCE: 2

```
Ser Thr Thr Lys Cys Thr Val Ser His Glu Val Ala Asp Cys Ser His
1               5                   10                  15

Leu Lys Leu Thr Gln Val Pro Asp Asp Leu Pro Thr Asn Ile Thr Val
            20                  25                  30

Leu Asn Leu Thr His Asn Gln Leu Arg Arg Leu Pro Ala Ala Asn Phe
        35                  40                  45

Thr Arg Tyr Ser Gln Leu Thr Ser Leu Asp Val Gly Phe Asn Thr Ile
    50                  55                  60

Ser Lys Leu Glu Pro Glu Leu Cys Gln Lys Leu Pro Met Leu Lys Val
65                  70                  75                  80

Leu Asn Leu Gln His Asn Glu Leu Ser Gln Leu Ser Asp Lys Thr Phe
                85                  90                  95

Ala Phe Cys Thr Asn Leu Thr Glu Leu His Leu Met Ser Asn Ser Ile
            100                 105                 110

Gln Lys Ile Lys Asn Asn Pro Phe Val Lys Gln Lys Asn Leu Ile Thr
        115                 120                 125

Leu Asp Leu Ser His Asn Gly Leu Ser Ser Thr Lys Leu Gly Thr Gln
    130                 135                 140

Val Gln Leu Glu Asn Leu Gln Glu Leu Leu Ser Asn Asn Lys Ile
145                 150                 155                 160

Gln Ala Leu Lys Ser Glu Glu Leu Asp Ile Phe Ala Asn Ser Ser Leu
                165                 170                 175

Lys Lys Leu Glu Leu Ser Ser Asn Gln Ile Lys Glu Phe Ser Pro Gly
            180                 185                 190
```

```
Cys Phe His Ala Ile Gly Arg Leu Phe Gly Leu Phe Leu Asn Asn Val
            195                 200                 205

Gln Leu Gly Pro Ser Leu Thr Glu Lys Leu Cys Leu Glu Leu Ala Asn
            210                 215                 220

Thr Ser Ile Arg Asn Leu Ser Leu Ser Asn Ser Gln Leu Ser Thr Thr
225                 230                 235                 240

Ser Asn Thr Thr Phe Leu Gly Leu Lys Trp Thr Asn Leu Thr Met Leu
            245                 250                 255

Asp Leu Ser Tyr Asn Asn Leu Asn Val Trp Leu Lys Cys Leu Glu His
            260                 265                 270

Leu Asn Met Glu Asp Asn Asp Ile Pro Gly Ile Lys Ser Asn Met Phe
            275                 280                 285

Thr Gly Leu Ile Asn Leu Lys Tyr Leu Ser Leu Ser Asn Ser Phe Thr
            290                 295                 300

Ser Leu Arg Thr Leu Thr Asn Glu Thr Phe Val Ser Leu Ala His Ser
305                 310                 315                 320

Pro Leu His Ile Leu Asn Leu Thr Lys Asn Lys Ile Ser Lys Ile Glu
            325                 330                 335

Ser Asp Ala Phe Ser Trp Leu Gly His Leu Glu Val Leu Asp Leu Gly
            340                 345                 350

Leu Asn Glu Ile Gly Gln Glu Leu Thr Gly Gln Glu Trp Arg Gly Leu
            355                 360                 365

Glu Asn Ile Phe Glu Ile Tyr Leu Ser Tyr Asn Lys Tyr Leu Gln Leu
            370                 375                 380

Thr Arg Asn Ser Phe Ala Leu Val Pro Ser Leu Gln Arg Leu Met Leu
385                 390                 395                 400

Arg Arg Val Ala Leu Lys Asn Val Asp Ser Ser Pro Ser Pro Phe Gln
            405                 410                 415

Pro Leu Arg Asn Leu Thr Ile Leu Asp Leu Ser Asn Asn Asn Ile Ala
            420                 425                 430

Asn Ile Asn Asp Asp Met Leu Glu Gly Leu Glu Lys Leu Glu Ile Leu
            435                 440                 445

Asp Leu Gln His Asn Asn Leu Ala Arg Leu Trp Lys His Ala Asn Pro
            450                 455                 460

Gly Gly Pro Ile Tyr Phe Leu Lys Gly Leu Ser His Leu His Ile Leu
465                 470                 475                 480

Asn Leu Glu Ser Asn Gly Phe Asp Glu Ile Pro Val Glu Val Phe Lys
            485                 490                 495

Asp Leu Phe Glu Leu Lys Ile Ile Asp Leu Gly Leu Asn Asn Leu Asn
            500                 505                 510

Thr Leu Pro Ala Ser Val Phe Asn Asn Gln Val Ser Leu Lys Ser Leu
            515                 520                 525

Asn Leu Gln Lys Asn Leu Ile Thr Ser Val Glu Lys Lys Val Phe Gly
            530                 535                 540

Pro Ala Phe Arg Asn Leu Thr Glu Leu Asp Met Arg Phe Asn Pro Phe
545                 550                 555                 560

Asp Cys Thr Cys Glu Ser Ile Ala Trp Phe Val Asn Trp Ile Asn Glu
            565                 570                 575

Thr His Thr Asn Ile Pro Glu Leu Ser Ser His Tyr Leu Cys Asn Thr
            580                 585                 590

Pro Pro His Tyr His Gly Phe Pro Val Arg Leu Phe Asp Thr Ser Ser
            595                 600                 605
```

```
Cys Lys Asp Ser Ala Pro Phe Glu
    610                 615
```

<210> SEQ ID NO 3
<211> LENGTH: 64
<212> TYPE: PRT
<213> ORGANISM: Homo sapiens

<400> SEQUENCE: 3

```
Val Gly Asn Asp Ser Phe Ala Trp Leu Pro Gln Leu Glu Tyr Phe Phe
1               5                   10                  15

Leu Glu Tyr Asn Asn Ile Gln His Leu Phe Ser His Ser Leu His Gly
            20                  25                  30

Leu Phe Asn Val Arg Tyr Leu Asn Leu Lys Arg Ser Phe Thr Lys Gln
        35                  40                  45

Ser Ile Ser Leu Ala Ser Leu Pro Lys Ile Asp Asp Phe Ser Phe Gln
    50                  55                  60
```

<210> SEQ ID NO 4
<211> LENGTH: 904
<212> TYPE: PRT
<213> ORGANISM: Homo sapiens

<400> SEQUENCE: 4

```
Met Arg Gln Thr Leu Pro Cys Ile Tyr Phe Trp Gly Gly Leu Leu Pro
1               5                   10                  15

Phe Gly Met Leu Cys Ala Ser Ser Thr Thr Lys Cys Thr Val Ser His
            20                  25                  30

Glu Val Ala Asp Cys Ser His Leu Lys Leu Thr Gln Val Pro Asp Asp
        35                  40                  45

Leu Pro Thr Asn Ile Thr Val Leu Asn Leu Thr His Asn Gln Leu Arg
    50                  55                  60

Arg Leu Pro Ala Ala Asn Phe Thr Arg Tyr Ser Gln Leu Thr Ser Leu
65                  70                  75                  80

Asp Val Gly Phe Asn Thr Ile Ser Lys Leu Glu Pro Glu Leu Cys Gln
            85                  90                  95

Lys Leu Pro Met Leu Lys Val Leu Asn Leu Gln His Asn Glu Leu Ser
            100                 105                 110

Gln Leu Ser Asp Lys Thr Phe Ala Phe Cys Thr Asn Leu Thr Glu Leu
        115                 120                 125

His Leu Met Ser Asn Ser Ile Gln Lys Ile Lys Asn Asn Pro Phe Val
    130                 135                 140

Lys Gln Lys Asn Leu Ile Thr Leu Asp Leu Ser His Asn Gly Leu Ser
145                 150                 155                 160

Ser Thr Lys Leu Gly Thr Gln Val Gln Leu Glu Asn Leu Gln Glu Leu
            165                 170                 175

Leu Leu Ser Asn Asn Lys Ile Gln Ala Leu Lys Ser Glu Glu Leu Asp
            180                 185                 190

Ile Phe Ala Asn Ser Ser Leu Lys Lys Leu Glu Leu Ser Ser Asn Gln
        195                 200                 205

Ile Lys Glu Phe Ser Pro Gly Cys Phe His Ala Ile Gly Arg Leu Phe
    210                 215                 220

Gly Leu Phe Leu Asn Asn Val Gln Leu Gly Pro Ser Leu Thr Glu Lys
225                 230                 235                 240

Leu Cys Leu Glu Leu Ala Asn Thr Ser Ile Arg Asn Leu Ser Leu Ser
            245                 250                 255
```

```
Asn Ser Gln Leu Ser Thr Thr Ser Asn Thr Thr Phe Leu Gly Leu Lys
            260                 265                 270

Trp Thr Asn Leu Thr Met Leu Asp Leu Ser Tyr Asn Asn Leu Asn Val
        275                 280                 285

Val Gly Asn Asp Ser Phe Ala Trp Leu Pro Gln Leu Glu Tyr Phe Phe
    290                 295                 300

Leu Glu Tyr Asn Asn Ile Gln His Leu Phe Ser His Ser Leu His Gly
305                 310                 315                 320

Leu Phe Asn Val Arg Tyr Leu Asn Leu Lys Arg Ser Phe Thr Lys Gln
                325                 330                 335

Ser Ile Ser Leu Ala Ser Leu Pro Lys Ile Asp Asp Phe Ser Phe Gln
            340                 345                 350

Trp Leu Lys Cys Leu Glu His Leu Asn Met Glu Asp Asn Asp Ile Pro
        355                 360                 365

Gly Ile Lys Ser Asn Met Phe Thr Gly Leu Ile Asn Leu Lys Tyr Leu
    370                 375                 380

Ser Leu Ser Asn Ser Phe Thr Ser Leu Arg Thr Leu Thr Asn Glu Thr
385                 390                 395                 400

Phe Val Ser Leu Ala His Ser Pro Leu His Ile Leu Asn Leu Thr Lys
                405                 410                 415

Asn Lys Ile Ser Lys Ile Glu Ser Asp Ala Phe Ser Trp Leu Gly His
            420                 425                 430

Leu Glu Val Leu Asp Leu Gly Leu Asn Glu Ile Gly Gln Glu Leu Thr
        435                 440                 445

Gly Gln Glu Trp Arg Gly Leu Glu Asn Ile Phe Glu Ile Tyr Leu Ser
    450                 455                 460

Tyr Asn Lys Tyr Leu Gln Leu Thr Arg Asn Ser Phe Ala Leu Val Pro
465                 470                 475                 480

Ser Leu Gln Arg Leu Met Leu Arg Arg Val Ala Leu Lys Asn Val Asp
                485                 490                 495

Ser Ser Pro Ser Pro Phe Gln Pro Leu Arg Asn Leu Thr Ile Leu Asp
            500                 505                 510

Leu Ser Asn Asn Asn Ile Ala Asn Ile Asn Asp Asp Met Leu Glu Gly
        515                 520                 525

Leu Glu Lys Leu Glu Ile Leu Asp Leu Gln His Asn Asn Leu Ala Arg
    530                 535                 540

Leu Trp Lys His Ala Asn Pro Gly Gly Pro Ile Tyr Phe Leu Lys Gly
545                 550                 555                 560

Leu Ser His Leu His Ile Leu Asn Leu Glu Ser Asn Gly Phe Asp Glu
                565                 570                 575

Ile Pro Val Glu Val Phe Lys Asp Leu Phe Glu Leu Lys Ile Ile Asp
            580                 585                 590

Leu Gly Leu Asn Asn Leu Asn Thr Leu Pro Ala Ser Val Phe Asn Asn
        595                 600                 605

Gln Val Ser Leu Lys Ser Leu Asn Leu Gln Lys Asn Leu Ile Thr Ser
    610                 615                 620

Val Glu Lys Lys Val Phe Gly Pro Ala Phe Arg Asn Leu Thr Glu Leu
625                 630                 635                 640

Asp Met Arg Phe Asn Pro Phe Asp Cys Thr Cys Glu Ser Ile Ala Trp
                645                 650                 655

Phe Val Asn Trp Ile Asn Glu Thr His Thr Asn Ile Pro Glu Leu Ser
            660                 665                 670

Ser His Tyr Leu Cys Asn Thr Pro Pro His Tyr His Gly Phe Pro Val
```

```
                        675                 680                 685
Arg Leu Phe Asp Thr Ser Ser Cys Lys Asp Ser Ala Pro Phe Glu Leu
    690                 695                 700

Phe Phe Met Ile Asn Thr Ser Ile Leu Leu Ile Phe Ile Phe Ile Val
705                 710                 715                 720

Leu Leu Ile His Phe Glu Gly Trp Arg Ile Ser Phe Tyr Trp Asn Val
                725                 730                 735

Ser Val His Arg Val Leu Gly Phe Lys Glu Ile Asp Arg Gln Thr Glu
            740                 745                 750

Gln Phe Glu Tyr Ala Ala Tyr Ile Ile His Ala Tyr Lys Asp Lys Asp
        755                 760                 765

Trp Val Trp Glu His Phe Ser Ser Met Glu Lys Glu Asp Gln Ser Leu
    770                 775                 780

Lys Phe Cys Leu Glu Glu Arg Asp Phe Glu Ala Gly Val Phe Glu Leu
785                 790                 795                 800

Glu Ala Ile Val Asn Ser Ile Lys Arg Ser Arg Lys Ile Ile Phe Val
                805                 810                 815

Ile Thr His His Leu Leu Lys Asp Pro Leu Cys Lys Arg Phe Lys Val
                820                 825                 830

His His Ala Val Gln Gln Ala Ile Glu Gln Asn Leu Asp Ser Ile Ile
            835                 840                 845

Leu Val Phe Leu Glu Glu Ile Pro Asp Tyr Lys Leu Asn His Ala Leu
        850                 855                 860

Cys Leu Arg Arg Gly Met Phe Lys Ser His Cys Ile Leu Asn Trp Pro
865                 870                 875                 880

Val Gln Lys Glu Arg Ile Gly Ala Phe Arg His Lys Leu Gln Val Ala
                885                 890                 895

Leu Gly Ser Lys Asn Ser Val His
                900

<210> SEQ ID NO 5
<211> LENGTH: 24
<212> TYPE: DNA
<213> ORGANISM: Artificial Sequence
<220> FEATURE:
<223> OTHER INFORMATION: Primer used to amplify TLR?64

<400> SEQUENCE: 5
gatctgtctc ataatggctt gtca                                          24

<210> SEQ ID NO 6
<211> LENGTH: 23
<212> TYPE: DNA
<213> ORGANISM: Artificial Sequence
<220> FEATURE:
<223> OTHER INFORMATION: Primer used to amplify TLR?64

<400> SEQUENCE: 6
gtttatcaat cctgtgaaca tat                                           23

<210> SEQ ID NO 7
<211> LENGTH: 50
<212> TYPE: DNA
<213> ORGANISM: Artificial Sequence
<220> FEATURE:
<223> OTHER INFORMATION: Primer used for in vitro mutagenesis to
      generate TLR3?64

<400> SEQUENCE: 7
```
cgatctttcc tacaacaact taaatgtgtg gctaaaatgt ttggagcacc        50

<210> SEQ ID NO 8
<211> LENGTH: 50
<212> TYPE: DNA
<213> ORGANISM: Artificial Sequence
<220> FEATURE:
<223> OTHER INFORMATION: Primer used for in vitro mutagenesis to
      generate TLR3?64

<400> SEQUENCE: 8
ggtgctccaa acattttagc cacacattta agttgttgta ggaaagatcg        50

<210> SEQ ID NO 9
<211> LENGTH: 2715
<212> TYPE: DNA
<213> ORGANISM: Homo sapiens

<400> SEQUENCE: 9
atgagacaga ctttgccttg tatctacttt tgggggggcc ttttgccctt tgggatgctg        60
tgtgcatcct ccaccaccaa gtgcactgtt agccatgaag ttgctgactg cagccacctg       120
aagttgactc aggtacccga tgatctaccc acaaacataa cagtgttgaa ccttacccat       180
aatcaactca agagattacc agccgccaac ttcacaaggt atagccagct aactagcttg       240
gatgtaggat ttaacaccat ctcaaaactg gagccagaat gtgccagaa acttcccatg       300 ttaaaagttt tgaacctcca gcacaatgag ctatctcaac tttctgataa aaccctttgcc       360 ttctgcacga atttgactga actccatctc atgtccaact caatccagaa aattaaaaat       420 aatcccttttg tcaagcagaa gaatttaatc acattagatc tgtctcataa tggcttgtca       480
tctacaaaat taggaactca ggttcagctg gaaaatctcc aagagcttct attatcaaac       540
aataaaattc aagcgctaaa aagtgaagaa ctggatatct ttgccaattc atctttaaaa       600
aaattagagt tgtcatcgaa tcaaattaaa gagttttctc agggtgtttt tcacgcaatt       660
ggaagattat ttggcctctt tctgaacaat gtccagctgg gtcccagcct tacagagaag       720 ctatgttttgg aattagcaaa cacaagcatt cggaatctgt ctctgagtaa cagccagctg       780
tccaccacca gcaatacaac tttcttggga ctaaagtgga caaatctcac tatgctcgat       840 cttttcctaca acaacttaaa tgtggttggt aacgattcct ttgcttggct tccacaacta       900
gaatatttct tcctagagta taataatata cagcatttgt tttctcactc tttgcacggg       960
cttttcaatg tgaggtacct gaatttgaaa cggtctttta ctaaacaaag tatttcccttt      1020 gcctcactcc ccaagattga tgattttttct tttcagtggc taaatgtttt ggagcacctt      1080
aacatggaag ataatgatat tccaggcata aaaagcaata tgttcacagg attgataaac      1140
ctgaaatact taagtctatc caactccttt acaagtttgc gaactttgac aaatgaaaca      1200
tttgtatcac ttgctcattc tcccttacac atactcaacc taaccaagaa taaaatctca      1260
aaaatagaga gtgatgcttt ctcttggttg ggccacctag aagtacttga cctgggcctt      1320
aatgaaattg ggcaagaact cacaggccag gaatggagag gtctagaaaa tatttttcgaa      1380 atctatcttt cctacaacaa gtacctgcag ctgactagga actcctttgc cttggtccca      1440
agccttcaac gactgatgct ccgaagggtg gccttaaaa atgtggatag ctctccttca      1500
ccattccagc tcttcgtaa cttgaccatt ctggatctaa gcaacaacaa catagccaac      1560
ataaatgatg acatgttgga gggtcttgag aaactagaaa ttctcgattt gcagcataac      1620
aacttagcac ggctctggaa acacgcaaac cctggtggtc ccatttattt cctaaagggt      1680

| | |
|---|---|
| ctgtctcacc tccacatcct taacttggag tccaacggct ttgacgagat cccagttgag | 1740 |
| gtcttcaagg atttatttga actaaagatc atcgatttag gattgaataa tttaaacaca | 1800 |
| cttccagcat ctgtctttaa taatcaggtg tctctaaagt cattgaacct tcagaagaat | 1860 |
| ctcataacat ccgttgagaa gaaggttttc gggccagctt tcaggaacct gactgagtta | 1920 |
| gatatgcgct ttaatccctt tgattgcacg tgtgaaagta ttgcctggtt tgttaattgg | 1980 |
| attaacgaga cccataccaa catccctgag ctgtcaagcc actacctttg caacactcca | 2040 |
| cctcactatc atgggttccc agtgagactt tttgatacat catcttgcaa agacagtgcc | 2100 |
| ccctttgaac tcttttcat gatcaatacc agtatcctgt tgatttttat ctttattgta | 2160 |
| cttctcatcc actttgaggg ctggaggata tcttttatt ggaatgtttc agtacatcga | 2220 |
| gttcttggtt tcaaagaaat agacagacag acagaacagt ttgaatatgc agcatatata | 2280 |
| attcatgcct ataagataa ggattgggtc tgggaacatt tctcttcaat ggaaaaggaa | 2340 |
| gaccaatctc tcaaattttg tctggaagaa agggactttg aggcgggtgt ttttgaacta | 2400 |
| gaagcaattg ttaacagcat caaaagaagc agaaaaatta ttttgttat aacacaccat | 2460 |
| ctattaaaag acccattatg caaaagattc aaggtacatc atgcagttca acaagctatt | 2520 |
| gaacaaaatc tggattccat tatattggtt ttccttgagg agattccaga ttataaactg | 2580 |
| aaccatgcac tctgtttgcg aagaggaatg tttaaatctc actgcatctt gaactggcca | 2640 |
| gttcagaaag aacggatagg tgcctttcgt cataaattgc aagtagcact tggatccaaa | 2700 |
| aactctgtac attaa | 2715 |

<210> SEQ ID NO 10
<211> LENGTH: 2523
<212> TYPE: DNA
<213> ORGANISM: Homo sapiens

<400> SEQUENCE: 10

| | |
|---|---|
| atgagacaga ctttgccttg tatctacttt tgggggggcc ttttgccctt tgggatgctg | 60 |
| tgtgcatcct ccaccaccaa gtgcactgtt agccatgaag ttgctgactg cagccacctg | 120 |
| aagttgactc aggtacccga tgatctaccc acaaacataa cagtgttgaa ccttaccccat | 180 |
| aatcaactca gaagattacc agccgccaac ttcacaaggt atagccagct aactagcttg | 240 |
| gatgtaggat ttaacaccat ctcaaaactg gagccagaat gtgccagaa acttcccatg | 300 |
| ttaaaagttt tgaacctcca gcacaatgag ctatctcaac tttctgataa aaccctttgcc | 360 |
| ttctgcacga atttgactga actccatctc atgtccaact caatccagaa attaaaaat | 420 |
| aatccctttg tcaagcagaa gaatttaatc acattagatc tgtctcataa tggcttgtca | 480 |
| tctacaaaat taggaactca ggttcagctg gaaaatctcc aagagcttct attatcaaac | 540 |
| aataaaattc aagcgctaaa aagtgaagaa ctggatatct ttgccaattc atcttttaaaa | 600 |
| aaattagagt tgtcatcgaa tcaaattaaa gagttttctc agggtgttt tcacgcaatt | 660 |
| ggaagattat ttggcctctt tctgaacaat gtccagctgg gtcccagcct tacagagaag | 720 |
| ctatgtttgg aattagcaaa cacaagcatt cggaatctgt ctctgagtaa cagccagctg | 780 |
| tccaccacca gcaatacaac tttcttggga ctaaagtgga caaatctcac tatgctcgat | 840 |
| ctttcctaca caacttaaa tgtgtggcta aatgtttgg agcaccttaa catggaagat | 900 |
| aatgatattc caggcataaa aagcaatatg ttcacaggat tgataaacct gaaatactta | 960 |
| agtctatcca actcctttac aagtttgcga actttgacaa atgaaacatt tgtatcactt | 1020 |
| gctcattctc ccttacacat actcaaccta accaagaata aatctcaaa aatagagagt | 1080 |

```
gatgctttct cttggttggg ccacctagaa gtacttgacc tgggccttaa tgaaattggg    1140
caagaactca caggccagga atggagaggt ctagaaaata ttttcgaaat ctatctttcc    1200
tacaacaagt acctgcagct gactaggaac tcctttgcct tggtcccaag ccttcaacga    1260
ctgatgctcc gaagggtggc ccttaaaaat gtggatagct ctccttcacc attccagcct    1320
cttcgtaact tgaccattct ggatctaagc aacaacaaca tagccaacat aaatgatgac    1380
atgttggagg gtcttgagaa actagaaatt ctcgatttgc agcataacaa cttagcacgg    1440
ctctggaaac acgcaaaccc tggtggtccc atttatttcc taagggtct gtctcacctc     1500 cacatcctta acttggagtc caacggcttt gacgagatcc cagttgaggt cttcaaggat    1560
ttatttgaac taaagatcat cgatttagga ttgaataatt aaacacact tccagcatct      1620 gtctttaata atcaggtgtc tctaaagtca ttgaaccttc agaagaatct cataacatcc    1680
gttgagaaga aggttttcgg gccagctttc aggaacctga ctgagttaga tatgcgcttt    1740 aatcccttg attgcacgtg tgaaagtatt gcctggtttg ttaattggat taacgagacc     1800
cataccaaca tccctgagct gtcaagccac tacctttgca acactccacc tcactatcat    1860
gggttcccag tgagactttt tgatacatca tcttgcaaag acagtgcccc ctttgaactc    1920
tttttcatga tcaataccag tatcctgttg atttttatct ttattgtact tctcatccac    1980
tttgagggct ggaggatatc ttttatttgg aatgtttcag tacatcgagt tcttggtttc    2040
aaagaaatag acagacagac agaacagttt gaatatgcag catatataat tcatgcctat    2100
aaagataagg attgggtctg ggaacatttc tcttcaatgg aaaaggaaga ccaatctctc    2160 aaatttgtc tggaagaaag ggactttgag gcgggtgttt ttgaactaga agcaattgtt     2220
aacagcatca aaagaagcag aaaaattatt tttgttataa cacaccatct attaaaagac    2280
ccattatgca aaagattcaa ggtacatcat gcagttcaac aagctattga acaaaatctg    2340
gattccatta tattggtttt ccttgaggag attccagatt ataaactgaa ccatgcactc    2400
tgtttgcgaa gaggaatgtt taaatctcac tgcatcttga actggccagt tcagaaagaa    2460
cggataggtg cctttcgtca taaattgcaa gtagcacttg atccaaaaa ctctgtacat      2520 taa                                                                  2523
```

<210> SEQ ID NO 11
<211> LENGTH: 350
<212> TYPE: PRT
<213> ORGANISM: Artificial Sequence
<220> FEATURE:
<223> OTHER INFORMATION: Wild type TLR3 polypeptide including a 64 amino
      acid Deletion corresponding to amino acids 289-353 of TLR3?64.
<220> FEATURE:
<221> NAME/KEY: unsure
<222> LOCATION: (135)
<223> OTHER INFORMATION: Wherein Xaa at position 135 can be any one of
      the twenty naturally occurring amino acids

<400> SEQUENCE: 11

Leu Lys Val Leu Asn Leu Gln His Asn Glu Leu Ser Gln Leu Ser Asp
 1               5                  10                  15

Lys Thr Phe Ala Phe Cys Thr Asn Leu Thr Glu Leu His Leu Met Ser
            20                  25                  30

Asn Ser Ile Gln Lys Ile Lys Asn Asn Pro Phe Val Lys Gln Lys Asn
        35                  40                  45

Leu Ile Thr Leu Asp Leu Ser His Asn Gly Leu Ser Ser Thr Lys Leu
    50                  55                  60

-continued

```
Gly Thr Gln Val Gln Leu Glu Asn Leu Gln Glu Leu Leu Leu Ser Asn
65                  70                  75                  80

Asn Lys Ile Gln Ala Leu Lys Ser Glu Glu Leu Asp Ile Phe Ala Asn
                85                  90                  95

Ser Ser Leu Lys Lys Leu Glu Leu Ser Ser Asn Gln Ile Lys Glu Phe
            100                 105                 110

Ser Pro Gly Cys Phe His Ala Ile Gly Arg Leu Phe Gly Leu Phe Leu
        115                 120                 125

Asn Asn Val Gln Leu Gly Xaa Ser Leu Thr Glu Lys Leu Cys Leu Glu
    130                 135                 140

Leu Ala Asn Thr Ser Ile Arg Asn Leu Ser Leu Ser Asn Ser Gln Leu
145                 150                 155                 160

Ser Thr Thr Ser Asn Thr Thr Phe Leu Gly Leu Lys Trp Thr Asn Leu
                165                 170                 175

Thr Met Leu Asp Leu Ser Tyr Asn Asn Leu Asn Val Val Gly Asn Asp
            180                 185                 190

Ser Phe Ala Trp Leu Pro Gln Leu Glu Tyr Phe Phe Leu Glu Tyr Asn
        195                 200                 205

Asn Ile Gln His Leu Phe Ser His Ser Leu His Gly Leu Phe Asn Val
    210                 215                 220

Arg Tyr Leu Asn Leu Lys Arg Ser Phe Thr Lys Gln Ser Ile Ser Leu
225                 230                 235                 240

Ala Ser Leu Pro Lys Ile Asp Asp Phe Ser Phe Gln Trp Leu Lys Cys
                245                 250                 255

Leu Glu His Leu Asn Met Glu Asp Asn Asp Ile Pro Gly Ile Lys Ser
            260                 265                 270

Asn Met Phe Thr Gly Leu Ile Asn Leu Lys Tyr Leu Ser Leu Ser Asn
        275                 280                 285

Ser Phe Thr Ser Leu Arg Thr Leu Thr Asn Glu Thr Phe Val Ser Leu
    290                 295                 300

Ala His Ser Pro Leu His Ile Leu Asn Leu Thr Lys Asn Lys Ile Ser
305                 310                 315                 320

Lys Ile Glu Ser Asp Ala Phe Ser Trp Leu Gly His Leu Glu Val Leu
                325                 330                 335

Asp Leu Gly Leu Asn Glu Ile Gly Gln Glu Leu Thr Gly Gln
            340                 345                 350
```